US010251533B2

(12) United States Patent
Dejima

(10) Patent No.: US 10,251,533 B2
(45) Date of Patent: Apr. 9, 2019

(54) OUTER TUBE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 646 days.

(21) Appl. No.: 14/868,393

(22) Filed: Sep. 29, 2015

(65) Prior Publication Data

US 2016/0022121 A1 Jan. 28, 2016

Related U.S. Application Data

(63) Continuation of application No. PCT/JP2014/058773, filed on Mar. 27, 2014.

(30) Foreign Application Priority Data

Mar. 29, 2013 (JP) .................................. 2013-074009

(51) Int. Cl.
*A61B 1/00* (2006.01)
*A61B 17/34* (2006.01)
(Continued)

(52) U.S. Cl.
CPC ...... *A61B 1/00154* (2013.01); *A61B 1/00137* (2013.01); *A61B 17/3415* (2013.01);
(Continued)

(58) Field of Classification Search
CPC .. A61M 2039/0633; A61M 2039/0646; A61M 2039/0653; A61M 2039/066;
(Continued)

(56) References Cited

U.S. PATENT DOCUMENTS 5,300,033 A 4/1994 Miller
5,496,289 A 3/1996 Wenstrom, Jr.
(Continued)

FOREIGN PATENT DOCUMENTS

JP 07-013301 3/1995
JP 07-509626 10/1995
(Continued)

OTHER PUBLICATIONS

"Written Opinion of the International Searching Authority of PCT/JP2014/058773", this report contains the following items: Form PCT/ISA237 (cover sheet), PCT/ISA237 (Box No. I), PCT/ISA237 (Box No. III), PCT/ISA237 (Box No. V) and PCT/ISA237 (Box No. VIII), dated Jun. 3, 2014, with English translation thereof, pp. 1-15.
(Continued)

*Primary Examiner* — Nathan R Price
*Assistant Examiner* — Anh Bui
(74) *Attorney, Agent, or Firm* — JCIPRNET

(57) ABSTRACT

The outer tube includes two insertion holes which are formed in a cross-sectional D-shape via a partition wall provided in the central part in a cross-section vertical to respective axial directions of the insertion holes. A slit of a valve body located in the insertion hole is disposed along reference line passing through centers of respective arcs of the insertion holes as seen from the axial directions of the insertion holes. Therefore, two leaflets of the slit abut on an arc edge of the insertion hole and a D-shaped cut part of the partition wall respectively when the insertion part of the treatment tool is internally fitted, and they are deformed into the same shape. Since there is no difference in stress applied to two leaflets, it is possible to secure the airtightness by the slit over a long period of time.

14 Claims, 21 Drawing Sheets

(51) Int. Cl.
  *A61M 39/22* (2006.01)
  *A61M 39/06* (2006.01)
  *A61B 34/30* (2016.01)

(52) U.S. Cl.
  CPC ...... *A61B 17/3421* (2013.01); *A61B 17/3462* (2013.01); *A61B 17/3498* (2013.01); *A61M 39/22* (2013.01); *A61B 2017/3441* (2013.01); *A61B 2017/3445* (2013.01); *A61B 2017/3464* (2013.01); *A61B 2017/3466* (2013.01); *A61B 2034/301* (2016.02); *A61M 2039/064* (2013.01); *A61M 2039/066* (2013.01); *A61M 2039/0633* (2013.01); *A61M 2039/0646* (2013.01); *A61M 2039/0653* (2013.01); *A61M 2039/0666* (2013.01)

(58) Field of Classification Search
  CPC .... A61M 2039/0666; A61M 2039/064; A61B 17/3462; A61B 17/3498; A61B 17/3464; A61B 17/3466; A61B 2034/301
  USPC ............ 604/93.01, 164.01, 164.02, 604/167.01–167.04
  See application file for complete search history.

(56) References Cited

U.S. PATENT DOCUMENTS

| 2005/0161048 | A1* | 7/2005 | Rapacki ............ A61M 16/0463 128/207.14 |
| 2009/0287163 | A1 | 11/2009 | Fischvogt et al. |
| 2010/0298775 | A1 | 11/2010 | Berry et al. |

FOREIGN PATENT DOCUMENTS

| JP | 11-342107 | 12/1999 |
| JP | 2009-297504 | 12/2009 |
| JP | 2010-269141 | 12/2010 |
| JP | 2012-170802 | 9/2012 |

OTHER PUBLICATIONS

"Office Action of Japan Counterpart Application," dated Aug. 30, 2016, p. 1-p. 7, with English translation thereof.
"Office Action of Japan Counterpart Application," dated Nov. 22, 2017, with English translation thereof, p. 1-p. 11.
"Office Action of Japan Counterpart Application," dated Jun. 11, 2018, with English translation thereof, p. 1-p. 6.

* cited by examiner

OUTER TUBE

CROSS-REFERENCE TO RELATED APPLICATIONS

This application is a Continuation of PCT International Application No. PCT/JP2014/058773 filed on Mar. 27, 2014, which claims priority under 35 U.S.C. § 119(a) to Japanese Patent Application No. 2013-074009 filed on Mar. 29, 2013. Each of the above application(s) is hereby expressly incorporated by reference, in its entirety, into the present application.

BACKGROUND OF THE INVENTION

Field of the Invention

The present invention relates to an outer tube, and particularly relates to an outer tube including two insertion holes in which an insertion part of an endoscope and an insertion part of a treatment tool can move back and forth.

Description of the Related Art

Endoscopic surgery to inset an endoscope and a treatment tool such as a laparoscope in an abdominal cavity through an outer tube tapped into an abdominal wall and treat a lesion site has become widespread in recent years. Since an operative wound in this endoscopic surgery is smaller than an abdominal surgery, it is possible to shorten a postoperative bed rest period.

In the endoscopic surgery, gas is supplied into the abdominal cavity beforehand to expand the abdominal cavity, and an observational region of the endoscope and a treatment region of the treatment tool are secured. Therefore, an airtight valve that prevents a gas leak is included in the outer tube.

Japanese National Publication of International Patent Application No. 7-509626 (hereinafter referred to as PTL 1) suggests a valve member (valve structure) which is provided in an outer tube (insertion instrument assembly) and in which a slit and opening (hole) forming an airtight valve are integrally configured. This valve member is disposed in a cap provided in the proximal end of an outer tube body (cannula). Here, the outer tube body in PTL 1 includes an insertion hole to move one treatment tool back and forth but does not include two insertion holes to move two treatment tools back and forth.

On the other hand, an outer tube disclosed in PTL 2 includes multiple insertion holes (lumens) in an outer tube body (body tube). According to this outer tube, since it is possible to insert multiple treatment tools by using the multiple insertion holes, it is possible to reduce the number of outer tubes tapped into an abdominal wall. By this means, it is possible to reduce invasion added to the body wall.

Moreover, an outer tube in Japanese Utility Model Laid-Open No. 7-13301 (hereinafter, referred to as PTL 2) can insert a treatment tool and an endoscope in one outer tube body.

In addition, in PTL 2, a cap is provided in the proximal end of the outer tube body, and a valve member including an elastic sheet is attached to this cap. The valve member includes a straight line (minus)-shaped slit in a position corresponding to each insertion hole. The insertion part of the treatment tool or the endoscope is internally fitted to the slit and moved backward relative to each insertion hole. When the insertion part is internally fitted to the slit, the slit closely contacts with the outside surface of the insertion part. Moreover, at the time of non-insertion (removal) at which the insertion part is not internally fitted to the slit, the slit is closed. By this means, since an airtight state is maintained, it is possible to prevent gas in a body cavity from leaking outside through the outer tube.

Furthermore, in a cross section vertical to the axial direction of the outer tube body, two insertion holes in PTL 2 are formed in a cross-sectional D-shaped (semicircle) via a partition wall formed in a straight shape in the central part. Further, the slit of the valve member in PTL 2 is formed in parallel to the partition wall.

SUMMARY OF THE INVENTION

By forming the cross-sectional shape of an insertion hole in a D-shape, the outer tube in PTL 2 makes the distance between the centers of two adjacent insertion holes shorter than the distance between centers in a case where two adjacent insertion holes are complete circles to decrease the diameter of the outer tube body and reduce invasion added to a body wall.

For the insertion hole of such a shape, a slit of the valve member in PTL 2 is formed in parallel to a partition wall as mentioned above. Therefore, two leaflets on both sides of the slit are elastically deformed when the insertion part is internally fitted to the slit, and one leaflet contacts with the above-mentioned partition wall of the insertion hole and the other leaflet contacts with the arc edge of the insertion hole. Therefore, since the deformed shapes of two leaflets are greatly different, that is, since the stresses caused in two leaflets are greatly different at the time of deformation, there is a problem that the elasticity of a leaflet with the larger stress decreases by fatigue by repetitive stress at early stage as compared with a leaflet with the smaller stress. Therefore, there is a case where it is not possible to secure the airtightness by the valve member at the early stage in PTL 2.

The present invention is made in view of such circumferences, and aims to provide an outer tube which can secure the airtightness over a long period of time.

In an aspect of the present invention, to achieve the above-mentioned object, there is provided an outer tube including: a penetration part configured to include a distal end, a proximal end and a longitudinal axis, and to penetrate a body wall; a first insertion hole in which a first insertion part of one of two medical instruments to be inserted inside the penetration part can be inserted in the inside of the penetration part along a direction parallel to the longitudinal axis so as to be freely movable back and forth; a second insertion hole which is disposed adjacent to the first insertion hole, and in which a second insertion part of another one of the two medical instruments can be inserted in the inside of the penetration part along a direction parallel to the first insertion hole so as to be freely movable back and forth; a first slit type airtight valve which is provided in the first insertion hole and includes a first slit configured to maintain airtightness when the first insertion part is removed from the first insertion hole; a second slit type airtight valve which is provided in the second insertion hole and includes a second slit configured to maintain airtightness when the second insertion part is removed from the second insertion hole; a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein: the first slit type airtight valve and the second slit type airtight valve are adjacently disposed via a partition wall, and, when the first slit type airtight valve and the second slit type airtight valve are projected on a surface orthogonal to the first insertion hole, the first slit type airtight valve and the second slit type airtight valve are formed in a line-symmetric shape centering on a reference line passing through a center of the first insertion hole and a center of the second insertion hole; a distance from the center of the first insertion hole to a wall core of the partition wall is formed to be shorter than a distance from the center of the first insertion hole to an edge part thereof on a side opposite to the partition wall, and a distance from the center of the second insertion hole to the wall core of the partition wall is formed to be shorter than a distance from the center of the second insertion hole to an edge part thereof on a side opposite to the partition wall; and the first slit and the second slit are disposed along the reference line in the surface orthogonal to the first insertion hole.

In an aspect of the present invention, to achieve the above-mentioned object, there is provided an outer tube including: a penetration part configured to include a distal end, a proximal end and a longitudinal axis, and to penetrate a body wall; a first insertion hole in which a first insertion part of one of two medical instruments to be inserted inside the penetration part can be inserted in the inside of the penetration part along a direction parallel to the longitudinal axis so as to be freely movable back and forth; a second insertion hole which is disposed adjacent to the first insertion hole via a partition wall, and in which a second insertion part of another one of the two medical instruments can be inserted in the inside of the penetration part along a direction parallel to the first insertion hole so as to be freely movable back and forth; a first slit type airtight valve which is provided in the first insertion hole and includes a first slit configured to maintain airtightness when the first insertion part is removed from the first insertion hole; a second slit type airtight valve which is provided in the second insertion hole and includes a second slit configured to maintain airtightness when the second insertion part is removed from the second insertion hole; a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein: when the first insertion hole and the second insertion hole are projected on a surface orthogonal to the first insertion hole, the first insertion hole and the second insertion hole are formed in a line-symmetric shape centering on a reference line passing through a center of the first insertion hole and a center of the second insertion hole, and, in the surface orthogonal to the first insertion hole, a distance from the center of the first insertion hole to a wall core of the partition wall is formed to be shorter than a distance from the center of the first insertion hole to an edge part thereof on a side opposite to the partition wall, and a distance from the center of the second insertion hole to the wall core of the partition wall is formed to be shorter than a distance from the center of the second insertion hole to an edge part thereof on a side opposite to the partition wall; and the first slit and the second slit are disposed along the reference line on the surface orthogonal to the first insertion hole.

Features of the outer tube of an aspect of the present invention are described below.

a) First Feature

The first slit type airtight valve and the second slit type airtight valve are adjacently disposed via a partition wall. Further, when the first slit type airtight valve and the second slit type airtight valve are projected on a surface orthogonal to the first insertion hole, they are formed in a line-symmetric shape centering on a reference line passing through the center of the first insertion hole and the center of the second insertion hole.

Alternatively, the first insertion hole and the second insertion hole which are provided in a penetration part are disposed via a partition wall. Further, when the first insertion hole and the second insertion hole are projected on a surface orthogonal to the first insertion hole, they are formed in a line-symmetric shape centering on a reference line passing through the center of the first insertion hole and the center of the second insertion hole.

Further, on the reference line, the first insertion hole and the second insertion hole are formed such that the distance from each center of the first insertion hole and the second insertion hole to the wall core of the partition wall is shorter than the distance from the center to the edge part thereof on the side opposite to the partition wall. By this means, since the distance between the centers of the first insertion hole and the second insertion hole is shorter than the distance between centers in a case where the first insertion hole and the second insertion hole are complete circles, it is possible to decrease the external diameter of a penetration part.

b) Second Feature

The first slit type airtight valve and the first opening type airtight valve are included in the first insertion hole, and the second slit type airtight valve and the second opening type airtight valve are included in the second insertion hole.

In the first insertion hole, since the first slit of the first slit type airtight valve closes when the first insertion part is removed, it is possible to secure the airtightness of the first insertion hole. Moreover, when the first insertion part is inserted in the first insertion hole, the first insertion part is internally fitted to the first opening of the first opening type airtight valve, that is, the inner peripheral edge of the first opening closely contacts with the outer peripheral surface of the first insertion part, and therefore it is possible to secure the airtightness of the first insertion hole.

In the second insertion hole, since the second slit of the second slit type airtight valve closes when the second insertion part is removed, it is possible to secure the airtightness of the second insertion hole. Moreover, when the second insertion part is inserted in the second insertion hole, the second insertion is internally fitted to the second opening of the second opening type airtight valve, that is, the inner peripheral edge of the second opening closely contacts with the outer peripheral surface of the second insertion part, and therefore it is possible to secure the airtightness of the second insertion hole.

c) Third feature Taking into account the first feature, the first slit and the second slit are disposed along a reference line in a surface orthogonal to the first insertion hole.

According to the aspect of the present invention, when the insertion part is internally fitted, two leaflets abut on the arc edge of the insertion hole and a partition wall respectively, and are deformed into the same shape. Therefore, since there is no difference in stress applied to two leaflets, it is possible to secure the airtightness by a slit over a longer period of time. Here, since two leaflets are deformed into the same shape, they smoothly return to the original shapes respectively when the insertion part is removed.

Here, "along a reference line" means "on the reference line", "a direction parallel to the reference line" or "a direction inclined by a slight angle with respect to the reference line", but it is preferable to be "on the reference line" to excellently obtain the operation and effect of the present invention.

In an aspect of the present invention, it is preferable that the partition wall is formed in a tabular shape.

In an aspect of the present invention, it is preferable that, when the first slit type airtight valve and the second slit type airtight valve are projected on the surface orthogonal to the first insertion hole, the first slit type airtight valve and the second slit type airtight valve are formed in a D-shape having a straight edge and an arc edge.

According to an aspect of the present invention, the D-shape can be exemplified as the shapes of the first insertion hole and the second insertion hole. However, the shapes of the first insertion hole and the second insertion hole are not limited to this. They may have any shapes which do not depart from the spirit of the present invention, for example, a semicircular shape.

In an aspect of the present invention, it is preferable that each of the first slit and the second slit has a cross shape, and a longer slit of two slits forming the cross-shaped slit functions as the first slit and the second slit.

According to an aspect of the present invention, the slit has a straight-line shape as a reference, but, in a case where the slip has a cross shape, the longer slit of two slits forming the cross-shaped slit functions as the first slit and the second slit.

In an aspect of the present invention, it is preferable that an insertion member having the first insertion hole and the second insertion hole is provided between the first slit type airtight valve and the first opening type airtight valve, and between the second slit type airtight valve and the second opening type airtight valve.

According to an aspect of the present invention, with respect to the insertion holes formed in the insertion member, when an insertion part is internally fitted, leaflets of slits are deformed to abut on the edge parts of the insertion holes respectively.

In an aspect of the present invention, it is preferable that: the outer tube further includes an introduction part an introduction part disposed in a proximal end of the penetration part, wherein the first slit type airtight valve, the second slit type airtight valve, the first opening type airtight valve, the second opening type airtight valve and the insertion member are provided in the introduction part.

According to an aspect of the present invention, a valve member including the first slit type airtight valve, the second slit type airtight valve, the first opening type airtight valve, the second opening type airtight valve and the insertion member is housed in the introduction part of the proximal end of the penetration part. By this means, it is possible to provide the valve member in the outer tube without increasing the external diameter of the penetration part, that is, without influencing invasion applied to a body wall.

In an aspect of the present invention, it is preferable that the first slit type airtight valve, the second slit type airtight valve, the first opening type airtight valve, the second opening type airtight valve and the insertion member are formed as an integrated unit valve body.

According to an aspect of the present invention, by forming the valve member as a unit valve body, the assemblablity of the valve member to the outer tube improves, and the handling of storage and management, and so on, of the valve member becomes easy.

In an aspect of the present invention, it is preferable that the first insertion part is an insertion part of an endoscope and the second insertion part is an insertion part of a treatment tool.

According to an aspect of the present invention, since the treatment tool and the endoscope can be inserted in the outer tube, it is possible to operate the endoscope by a surgeon who operates the treatment tool. By this means, a scopist who operates the endoscope becomes unnecessary. Therefore, it is possible to solve a problem that surgeon's hands and scopist's hands interfere with each other above patient's abdominal wall. Further, since the work space of the surgeon becomes wide, the surgery operability improves.

In an aspect of the present invention, it is preferable that a diameter of the first opening of the first opening type airtight valve is larger than a diameter of the second opening of the second opening type airtight valve.

Generally, since an optical system including multiple lenses and a built-in element such as a signal cable are inserted in the insertion part of the endoscope, the external diameter of the insertion part of the endoscope is larger than the external diameter of the insertion part of the treatment tool. According to an aspect of the present invention, in this case, the diameter of the first opening of the first opening type airtight valve to which the insertion part of the endoscope is internally fitted is made larger than the diameter of the second opening of the second opening type airtight valve to which the insertion part of the treatment tool is internally fitted.

In an aspect of the present invention, it is preferable that the first slit type airtight valve and the second opening type airtight valve are integrally formed, and the second slit type airtight valve and the first opening type airtight valve are integrally formed.

According to an aspect of the present invention, the first slit type airtight valve and the second opening type airtight valve are integrated, and the second slit type airtight valve and the first opening type airtight valve are integrated. Therefore, it is possible to reduce the number of parts of the valve member. Moreover, the assemblability of the valve member to the outer tube improves, and the handling of storage and management, and so on, of the valve member becomes also easy.

In an aspect of the present invention, it is preferable that the first slit type airtight valve and the second slit type airtight valve are integrally formed, and the first opening type airtight valve and the second opening type airtight valve are integrally formed.

According to an aspect of the present invention, the first slit type airtight valve and the second slit type airtight valve are integrated, and the first opening type airtight valve and the second opening type airtight valve are integrated. Therefore, it is possible to reduce the number of parts of the valve member. Moreover, the assemblability of the valve member to the outer tube improves, and the handling of storage and management, and so on, of the valve member becomes also easy.

In an aspect of the present invention, there is provided an outer tube including: a penetration part configured to include a distal end, a proximal end and a longitudinal axis, and to penetrate a body wall; a first insertion hole in which a first insertion part of one of two medical instruments to be inserted inside the penetration part can be inserted in the inside of the penetration part along a direction parallel to the longitudinal axis so as to be freely movable back and forth; a second insertion hole which is disposed adjacent to the first insertion hole, and in which a second insertion part of another one of the two medical instruments can be inserted in the inside of the penetration part along a direction parallel to the first insertion hole so as to be freely movable back and forth; a first slit type airtight valve which is provided in the first insertion hole and includes a first slit configured to maintain airtightness when the first insertion part is removed from the first insertion hole; a second slit type airtight valve which is provided in the second insertion hole and includes a second slit configured to maintain airtightness when the second insertion part is removed from the second insertion hole; a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein: the first slit type airtight valve and the second slit type airtight valve are disposed in mutually shifted positions in an axial direction of the longitudinal axis of the penetration part.

According to an aspect of the present invention, the opening and closing operation of one slit type airtight valve does not influence the opening and closing operation of the other slit type airtight valve.

In an aspect of the present invention, it is preferable that the first slit type airtight valve and the second opening type airtight valve are integrally formed, and the second slit type airtight valve and the first opening type airtight valve are integrally formed.

According to an aspect of the present invention, it is possible to reduce the number of parts of the valve member. Moreover, the assemblability of the valve member to the outer tube improves, and the handling of storage and management, and so on, of the valve member becomes also easy.

In an aspect of the present invention, there is provided an outer tube including: a penetration part configured to include a distal end, a proximal end and a longitudinal axis, and to penetrate a body wall; a first insertion hole in which a first insertion part of one of two medical instruments to be inserted inside the penetration part can be inserted in the inside of the penetration part along a direction parallel to the longitudinal axis so as to be freely movable back and forth; a second insertion hole which is disposed adjacent to the first insertion hole via a partition wall, and in which a second insertion part of another one of the two medical instruments can be inserted in the inside of the penetration part along a direction parallel to the first insertion hole so as to be freely movable back and forth; a first slit type airtight valve which is provided in the first insertion hole and includes a first slit configured to maintain airtightness when the first insertion part is removed from the first insertion hole; a second slit type airtight valve which is provided in the second insertion hole and includes a second slit configured to maintain airtightness when the second insertion part is removed from the second insertion hole; a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein: the first insertion hole and the second insertion hole have a major axis and a minor axis in a cross-section orthogonal to the longitudinal axis of the penetration part, and the first slit and the second slit are formed along the minor axis.

According to an aspect of the present invention, respective leaflets of the first slit and the second slit are elastically deformed in the major axis direction of the first insertion hole and the second insertion hole. That is, the load (stress) at the elastic deformation of the leaflets is mitigated as compared with a case where the leaflets are elastically deformed in the minor axis direction in which the elastic deformation amounts of the leaflets are restricted more than the major axis direction. Therefore, the service life of the first slit type airtight valve and the second slit type airtight valve is made longer.

According to the present invention, it is possible to provide an outer tube which can secure the airtightness over a long period of time.

DETAILED DESCRIPTION OF THE EMBODIMENTS

In the following, a preferable embodiment of an outer tube of the present invention is described in detail according to the accompanying drawings.

Figure 1:
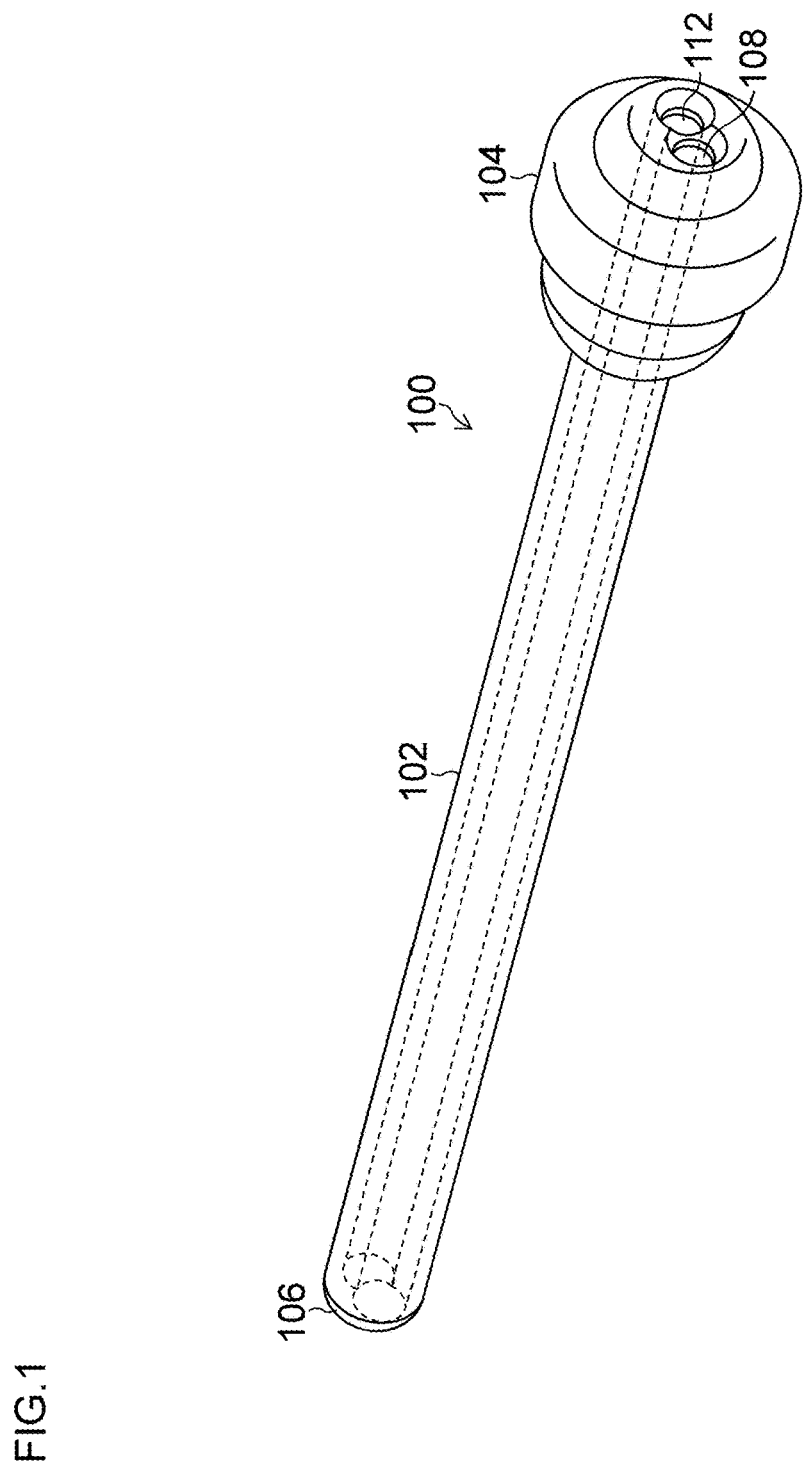
FIG. 1 is the schematic configuration diagram of an outer tube of an embodiment.
Figure 2:
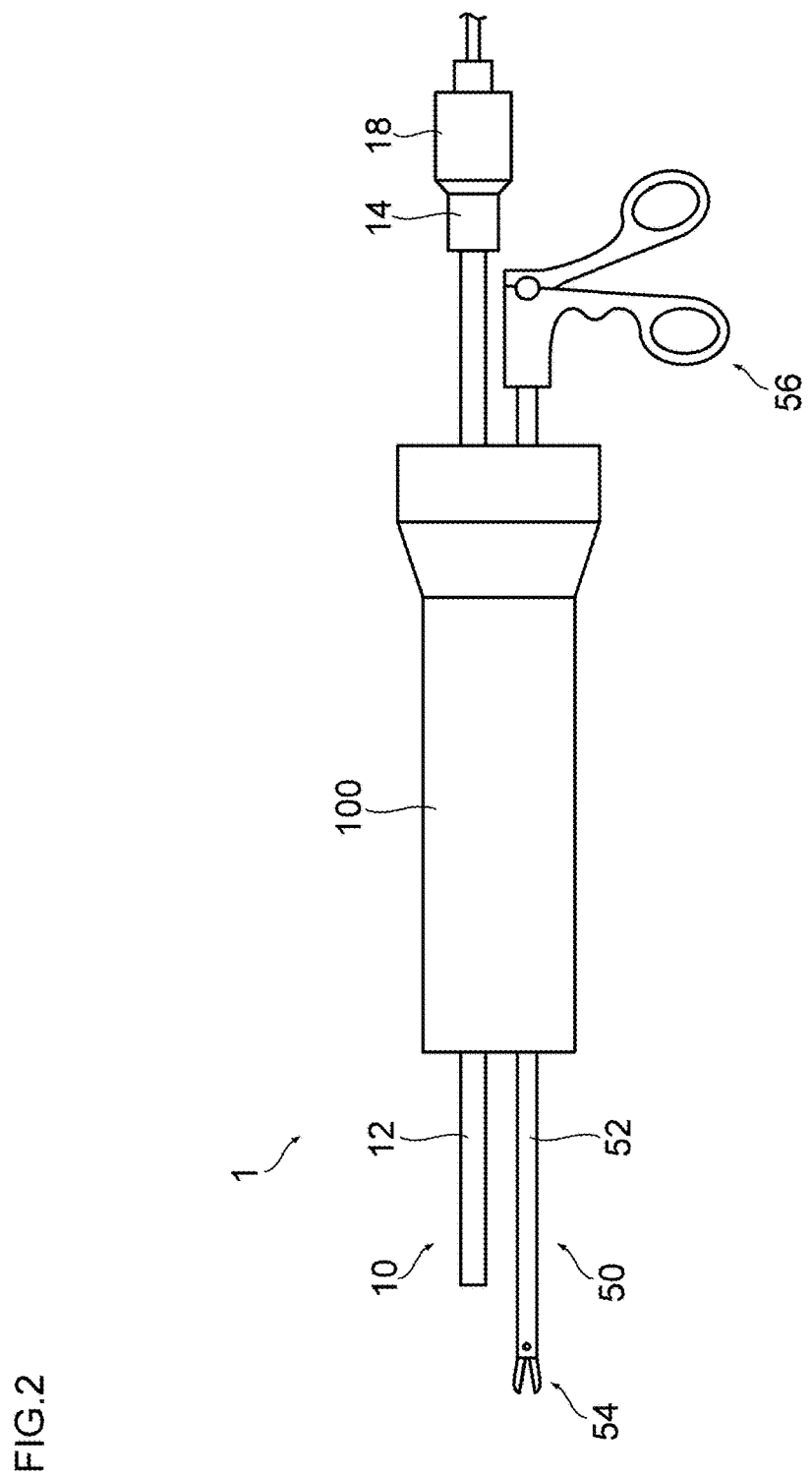
FIG. 2 is a schematic configuration diagram of an endoscopic surgery device including the outer tube in FIG. 1.

FIG. 1 is an external view of an outer tube 100 according to an embodiment, and FIG. 2 is a schematic configuration diagram of an endoscopic surgery device 1, which illustrates a use mode of the outer tube 100.

<<Configuration of Endoscopic Surgery Device 1>>

The endoscopic surgery device 1 includes an endoscope 10 which is inserted in patient's body cavity to perform observation in the body cavity, a treatment tool 50 which is inserted in patient's body cavity to perform necessary treatment, and the outer tube 100 that guides the endoscope 10 and the treatment tool 50 into patient's body cavity.

<Endoscope 10>

Figure 3:
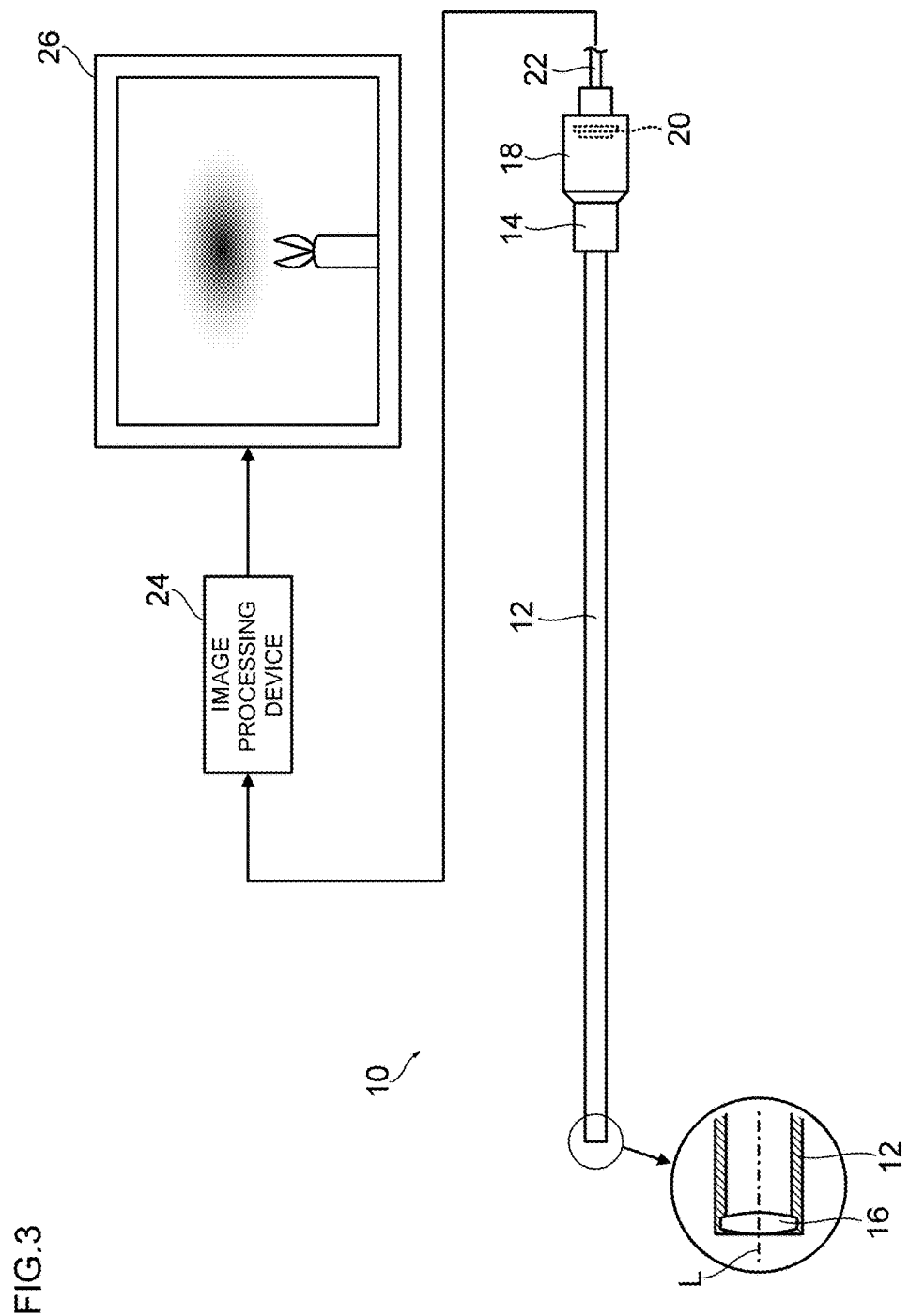
FIG. 3 is a schematic configuration diagram illustrating one example of an endoscope.

FIG. 3 is a schematic configuration diagram illustrating one example of the endoscope 10.

The endoscope 10 is a direct-view-type rigid endoscope such as a laparoscope. The endoscope 10 includes a straight insertion part 12 to be inserted in patient's body cavity and an eyepiece part 14 disposed in the proximal end of the insertion part 12.

An object lens 16 is disposed in the distal end of the insertion part 12. An ocular lens (not illustrated) is disposed in the eyepiece part 14. Multiple relay lens (not illustrated) is disposed inside the insertion part 12. An image made by the object lens is observed by the ocular lens through the relay lens.

Here, an optical axis L of the object lens 16 is disposed in parallel to an axis of the insertion part 12 (the same applies to the ocular lens and the relay lens). Therefore, the image of an object facing the distal end surface of the insertion part 12 is observed in the eyepiece part 14.

A TV camera 18 that images a part or whole of an observation image of the endoscope 10 is attached to the eyepiece part 14. An imaging element (for example, a CCD (Charge Coupled Device) and a CMOS (Complementary Metal-Oxide Semiconductor), and so on) 20 that is imaging means is built into this TV camera 18. By this means, it is possible to image the part or whole of the image (the observation image of the endoscope 10) observed by the eyepiece part 14 of the endoscope 10 by the imaging element.

The TV camera 18 is connected with an image processing device 24 through a cable 22 having flexibility. The image processing device 24 imports a signal output from the imaging element 20, performs various kinds of processing on the imported signal and generates a video signal that can be output to a display 26.

The display 26 such as a liquid crystal monitor is connected with the image processing device 24. The video signal generated in the image processing device 24 is output to the display 26 and displayed on the screen of the display 26 as an endoscopic image.

Here, illumination means is not included in the endoscope 10 of this example. Illumination is performed by another means, for example, needle light. The diameter of the insertion part of the endoscope can be reduced by omitting the illumination means built into the endoscope. By this means, the diameter of the outer tube 100 can also be reduced, and it is possible to decrease invasion added to patient's body wall. Here, the endoscope 10 is not limited to the relay lens system, and it may be an endoscope in which imaging means is installed in the distal end part of the insertion part 12.

<Needle Light 30>

Figure 4:
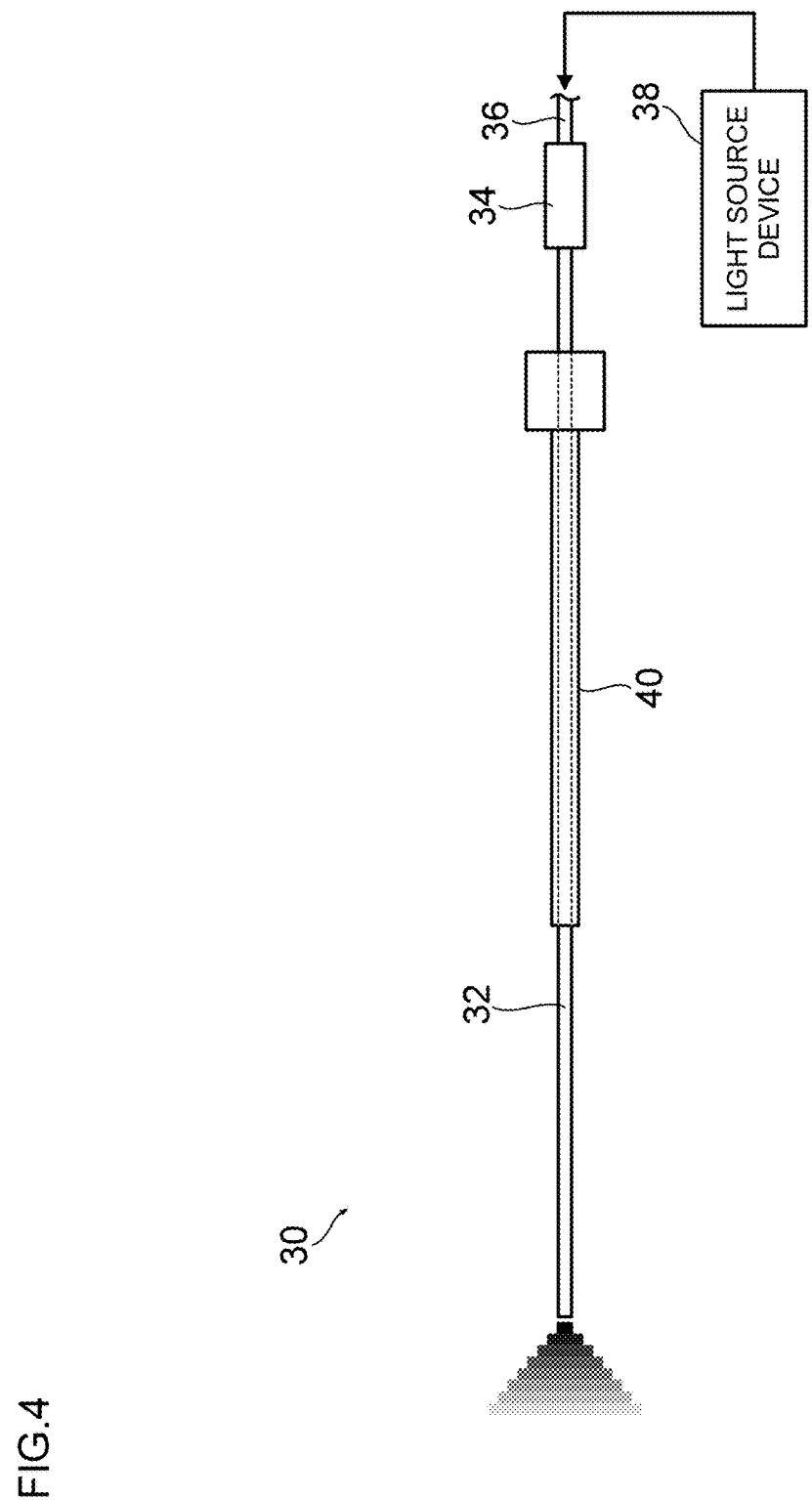
FIG. 4 is a schematic configuration diagram illustrating one example of needle light.

FIG. 4 is a schematic configuration diagram illustrating one example of the needle light 30.

The needle light 30 is inserted in patient's body cavity and irradiates the inside of the body cavity by illumination light.

The needle light 30 has a straight rod-shaped insertion part 32. An illumination window (not illustrated) is included in the distal end of the insertion part 32, and illumination light is irradiated from this illumination window to the axial direction.

An optical fiber bundle that transmits the illumination light irradiated from the illumination window is housed in the insertion part 32.

A connection part 34 is included in the proximal end of the needle light 30. A light source device 38 is connected with the connection part 34 through a cable 36 having flexibility. The illumination light emitted from the illumination window is supplied from the light source device 38.

As one example, the needle light 30 is inserted in the body cavity through an outer tube 40 for needle light.

<Treatment Tool 50>

Figure 5:
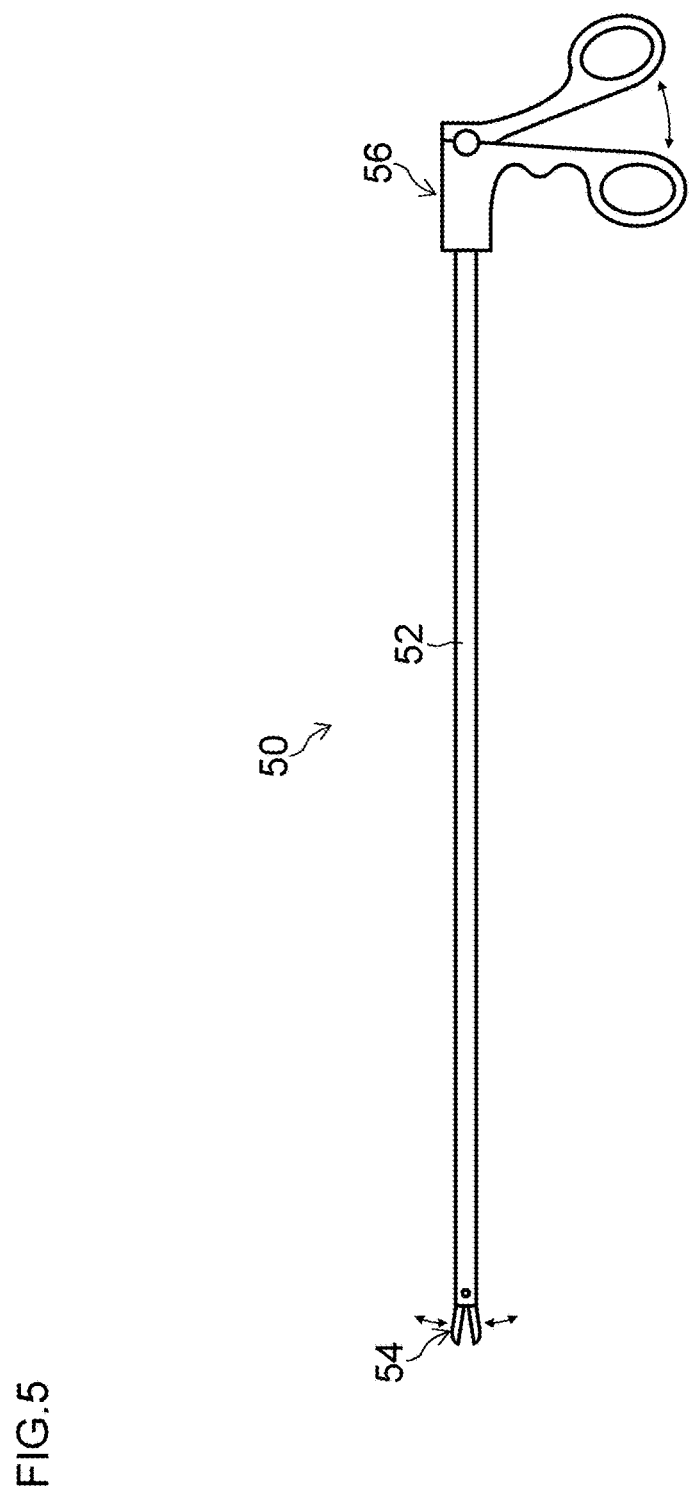
FIG. 5 is a schematic configuration diagram illustrating one example of a treatment tool.

FIG. 5 is a schematic configuration diagram illustrating one example of the treatment tool 50.

The treatment tool 50 includes a straight insertion part 52 to be inserted in the body cavity, a treatment part 54 disposed in the distal end of the insertion part 52 and a handle part (operation unit) 56 disposed in the proximal end of the insertion part 52. The treatment part 54 illustrated in FIG. 5 is assumed to have a scissors structure, and the treatment part 54 is operated to open and close by the opening and closing operation of the handle part 56.

Here, the treatment tool 50 is not limited to this, and a forceps, a laser probe, a suture instrument, a radio knife, a needle holder and an ultrasonic aspirator, and so on, can be used as a treatment tool.

<Outer Tube 100>

The outer tube 100 illustrated in FIG. 1 is tapped into patient's body cavity wall and guides the endoscope 10 and the treatment tool 50 into patient's body cavity.

Figure 6:
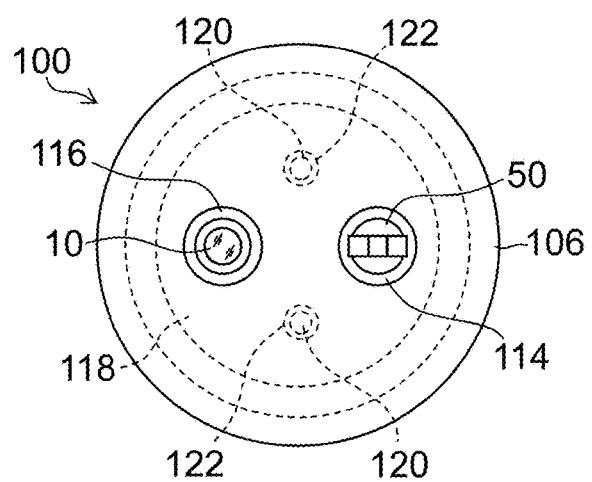
FIG. 6 is a front view of an outer tube in which an endoscope and a treatment tool are inserted.
Figure 7:
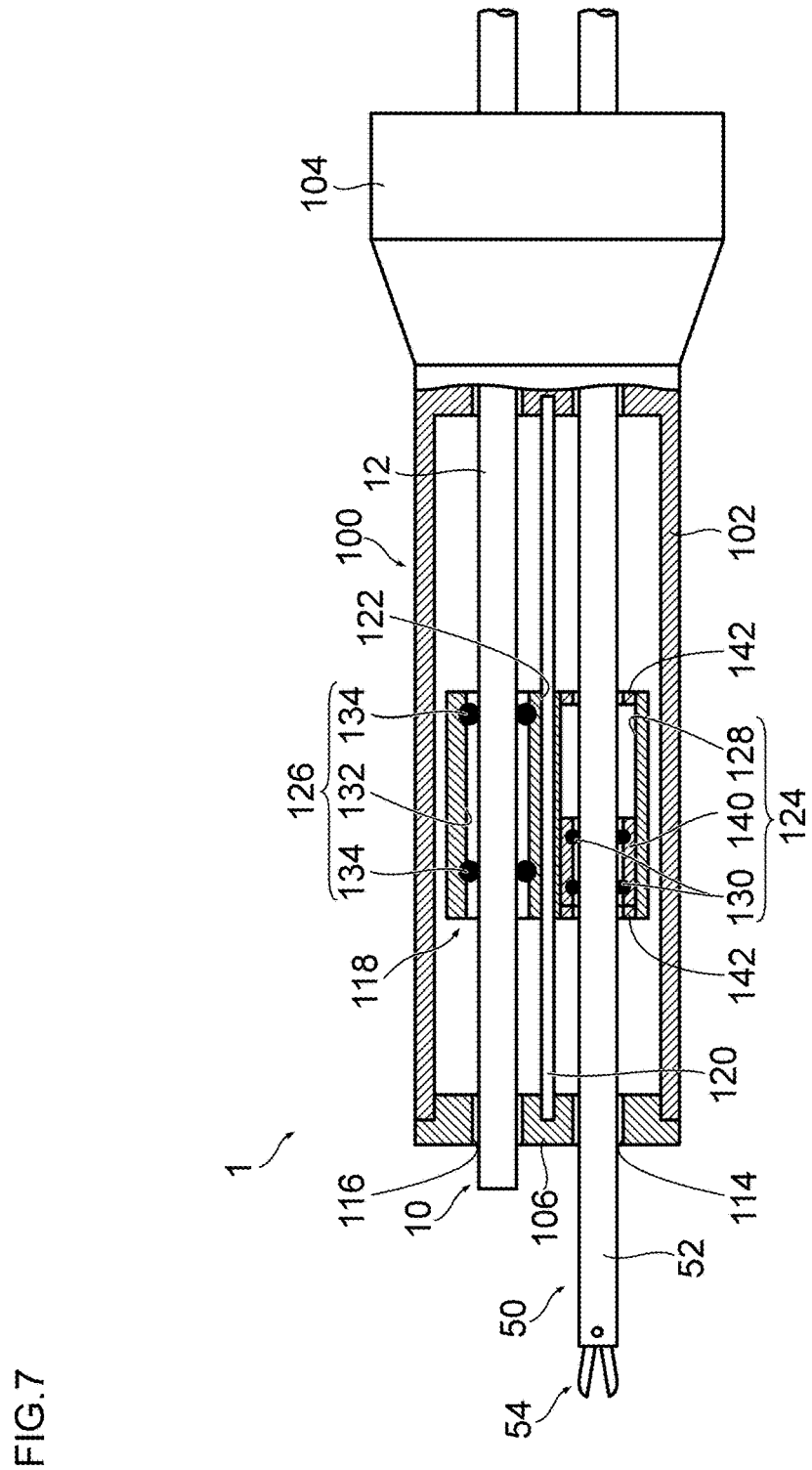
FIG. 7 is a side partial sectional view of an outer tube in which an endoscope and a treatment tool are inserted.
Figure 8:
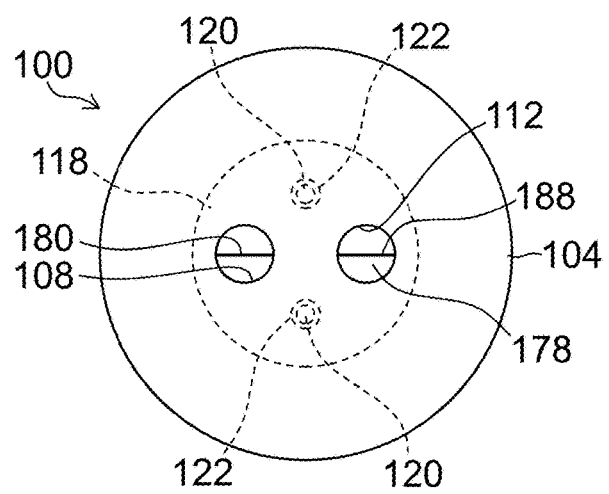
FIG. 8 is a rear view of an outer tube.

FIG. 6 is a front view of the outer tube 100 in which the endoscope 10 and the treatment tool 50 are inserted, FIG. 7 is a side partial sectional view of the outer tube 100 in which the endoscope 10 and the treatment tool 50 are inserted, and FIG. 8 is a rear view of the outer tube 100.

The outer tube 100 includes a cylindrical outer tube body (penetration part) 102 having a longitudinal axis. A cap (introduction part) 104 is attached to the proximal end of the outer tube body 102. A valve member 160 (see FIG. 11) of an embodiment described later is housed and disposed in the cap 104. The proximal end opening portion of the outer tube body 102 is occluded by the valve member 160 disposed in the cap 104. A cap 106 is attached to the distal end of the outer tube body 102. The distal end opening portion of the outer tube body 102 is occluded by the cap 106.

As illustrated in FIGS. 1 and 8, a treatment tool entry port 108 through which the insertion part 52 of the treatment tool 50 inserted in the outer tube body 102 is provided in the cap 104. The treatment tool entry port 108 is formed to have an internal diameter corresponding to the external diameter of the insertion part 52 of the used treatment tool 50.

Moreover, an endoscope entry port 112 through which the insertion part 12 of the endoscope 10 is inserted in the outer tube body 102 is provided in the cap 104. The endoscope entry port 112 is formed to have an internal diameter corresponding to the external diameter of the insertion part 12 of the used endoscope 10.

As illustrated in FIG. 6, the cap 106 is provided with a treatment tool exit port 114 from which the insertion part 52 of the treatment tool 50 inserted in the outer tube body 102 is delivered. The treatment tool exit port 114 is formed to have an internal diameter corresponding to the external diameter of the insertion part 52 of the used treatment tool 50. The treatment tool entry port 108 in FIG. 8 and the treatment tool exit port 114 in FIG. 6 are disposed on the same axis which is parallel to the axis of the outer tube body 102. By this means, like FIG. 7, the treatment tool 50 inserted from the treatment tool entry port 108 (see FIG. 8) is delivered from the treatment tool exit port 114 (see FIG. 6). At this time, the insertion part 52 of the treatment tool 50 is delivered with a posture parallel to the axis of the outer tube body 102.

Moreover, the cap 106 in FIG. 6 is provided with an endoscope exit port 116 from which the insertion part 12 of the endoscope 10 inserted in the outer tube body 102 from the endoscope entry port 112 in FIG. 8 is delivered. The endoscope exit port 116 is formed to have an internal diameter corresponding to the external diameter of the insertion part 12 of the used endoscope 10. The endoscope entry port 112 (see FIG. 8) and the endoscope exit port 116 (see FIG. 6) are disposed on the same axis which is parallel to the axis of the outer tube body 102. By this means, like FIG. 7, the endoscope 10 inserted from the endoscope entry port 112 (see FIG. 8) is delivered from the endoscope exit port 116 (see FIG. 6). At this time, the insertion part 12 of the endoscope 10 is delivered with a posture parallel to the axis of the outer tube body 102.

<Internal Structure of Outer Tube 100>

As illustrated in FIG. 7, a slider 118 that is movable in a direction parallel to the axis of the outer tube body 102 is provided inside the outer tube body 102.

The slider 118 is formed in a columnar shape, which can be housed in the outer tube body 102. The slider 118 is installed so as to be guided by a pair of guide shafts 120 and be movable in the outer tube body 102 in a direction parallel to the axis of the outer tube body 102.

Respective guide shafts 120 have a round rod shape and are disposed inside the outer tube body 102 in parallel to each other (see FIG. 6). Moreover, proximal ends of the guide shafts 120 are supported by the cap 104, and distal ends of the guide shafts 120 are supported by the cap 106. The guide shafts 120 are disposed in parallel to the axis of the outer tube body 102.

A pair of guide holes 122 in which the pair of guide shafts 120 can be inserted are included in the slider 118. The pair of guide holes 122 is disposed at the same interval as the disposition interval of the pair of guide shafts 120, and they are formed in parallel to the axis of the outer tube body 102. The guide shafts 120 are inserted in the guide holes 122 and the slider 118 is guided by the guide shaft 120.

The slider 118 includes a treatment tool holding part 124 which holds the insertion part 52 of the treatment tool 50 inserted in the outer tube body 102, and an endoscope holding part 126 which holds the insertion part 12 of the endoscope 10 inserted in the outer tube body 102.

The endoscope holding part 126 includes an endoscope holding hole 132 inserted in the insertion part 12 of the endoscope 10 and a pair of O-rings 134 disposed in the endoscope holding hole 132.

The endoscope holding hole 132 is formed penetrating the slider 118. The endoscope holding hole 132 is formed in parallel to the axis of the outer tube body 102 and is disposed on the same axis as the endoscope entry port 112 and the endoscope exit port 116.

The pair of O-rings 134 is attached to two front and rear positions inside the endoscope holding hole 132. The internal diameter of the O-rings 134 is formed to be slightly smaller than the external diameter of the insertion part 12 of the endoscope 10.

The insertion part 12 of the endoscope 10 inserted from the endoscope entry port 112 into the outer tube body 102 passes through the endoscope holding hole 132 and is delivered from the endoscope exit port 116. When passing through the endoscope holding hole 132, the endoscope 10 passes through the O-rings 134. As mentioned above, the internal diameter of the O-rings 134 is formed to be slightly smaller than the external diameter of the insertion part 12 of the endoscope 10. Therefore, when passing though the endoscope holding hole 132, the insertion part 12 of the endoscope 10 is held to the endoscope holding hole 132 by the elastic force of the O-rings 134.

Here, since the holding here denotes holding by the elastic force of the O-rings 134, it is possible to arbitrarily adjust the holding position of the endoscope 10 with respect to the slider 118.

Moreover, the endoscope 10 is held by the elastic force of the O-rings 134, but the friction force between the O-rings 134 and the insertion part 12 of the endoscope 10 is set to be greater than the friction force between the guide shafts 120 and the guide hole 122 (=the friction force between the outer tube body 102 and the slider 118). By this means, the slider 118 and the endoscope 10 integrally move with respect to the outer tube body 102.

The treatment tool holding part 124 includes a treatment tool holding hole 128 in which the insertion part 52 of the treatment tool 50 is inserted, a sleeve 140 which is disposed in the treatment tool holding hole 128 and moves in an axial direction along the treatment tool holding hole 128, and a pair of O-rings 130 disposed in the sleeve 140.

The treatment tool holding hole 128 is formed penetrating the slider 118. The treatment tool holding hole 128 is formed in parallel to the axis of the outer tube body 102 and is disposed on the same axis as the treatment tool entry port 108 and the treatment tool exit port 114.

A circular stopper ring 142 is attached to both end portions of the treatment tool holding hole 128. The sleeve 140 housed in the treatment tool holding hole 128 is prevented from being detached from the treatment tool holding hole 128 by the stopper rings 142 and 142. Moreover, as for the sleeve 140, the movable amount (allowance amount) in the axial direction is set by the stopper rings 142 and 142. That is, the sleeve 140 is provided between the stopper rings 142 and 142 provided in both ends of the treatment tool holding hole 128 so as to be movable with respect to the slider 118.

The sleeve 140 is formed in a cylindrical shape, housed inside the treatment tool holding hole 128 and disposed on the same axis as the treatment tool holding hole 128. That is, the sleeve 140 is disposed on the same axis as the treatment tool entry port 108 and the treatment tool exit port 114. By this means, when the treatment tool 50 is inserted from the treatment tool entry port 108 along the axial direction, the insertion part 52 of the treatment tool 50 is inserted in the inner peripheral part of the sleeve 140.

The pair of O-rings 130 is attached to two front and rear positions inside the sleeve 140. The internal diameter of this O-rings 130 is formed to be slightly smaller than the external diameter of the insertion part 52 of the treatment tool 50.

The insertion part 52 of the treatment tool 50 inserted from the treatment tool entry port 108 into the outer tube body 102 passes through the treatment tool holding hole 128 and is delivered from the treatment tool exit port 114. When passing through the treatment tool holding hole 128, the insertion part 52 passes through the O-rings 130 disposed in the inner peripheral part of the sleeve 140. The internal diameter of the O-rings 130 is formed to be slightly smaller than the external diameter of the insertion part 52 of the treatment tool 50. Therefore, when passing through the O-rings 130, the insertion part 52 is held to the sleeve 140 by the elastic force of the O-rings 130.

Here, since the holding here denotes holding by the elastic force of the O-rings 130, it is possible to arbitrarily adjust the holding position of the treatment tool 50 with respect to the sleeve 140. That is, it is possible to arbitrarily adjust the holding position of the treatment tool 50 with respect to the slider 118.

In the treatment tool holding part 124, the sleeve 140 and the treatment tool 50 are integrated, and the sleeve 140 moves in interlock with the movement of the treatment tool 50.

Here, in a case where the friction force (F3) between the sleeve 140 and the treatment tool holding hole 128 is greater than the friction force (F2) between the insertion part 52 of the treatment tool 50 and the O-rings 130, the insertion part 52 slides between the O-rings 130 and the sleeve 140 cannot be moved with respect to the slider 118. For such reasons, the friction force (F3) between the sleeve 140 and the treatment tool holding hole 128 is set to be less than the friction force (F2) between the treatment tool 50 and the O-rings 130.

Meanwhile, in a case where the friction force (F3) between the sleeve 140 and the treatment tool holding hole 128 is greater than that the friction force (=the friction force between the outer tube body 102 and the slider 118: F1) between the guide shafts 120 and the guide holes 122, when the treatment tool 50 is moved, the slider 118 moves with respect to the outer tube body 102 instead of the sleeve 140. For such reasons, the friction force (F1) between the guide shafts 120 and the guide holes 122 is set to be greater than the friction force (F3) between the sleeve 140 and the treatment tool holding hole 128.

Moreover, the friction force (F2) between the treatment tool 50 and the O-rings 130 is set to be greater than the friction force (F1) between the guide shafts 120 and the guide holes 122.

That is, the relationship among the friction force (F1) between the guide shafts 120 and the guide holes 122, the friction force (F2) between the treatment tool 50 and the O-rings 130, and the friction force (F3) between the sleeve 140 and the treatment tool holding hole 128 is set to F2>F1>F3.

By this means, when the insertion part 52 of the treatment tool 50 is moved in the axial direction, the slider 118 does not move if slider 118 moves within a movable amount (allowance amount) set by a pair of stopper rings 142 and 142. That is, the endoscope 10 is not interlocked with the movement of the insertion part 52 within the range of the movable amount. Thus, the outer tube 100 has "allowance" for the movement of the treatment tool 50.

By giving the "allowance" to the outer tube 100, for example, it is possible to prevent an image on a screen from shaking in a case where the insertion part 52 is minutely displaced in the axial direction (in a case where the back-and-forth movement operation of low amplitude is performed). Therefore, it is possible to provide an image which can be easily seen without shake.

<<Operation of Endoscopic Surgery Device 1>>

First, the insertion part 12 of the endoscope 10 is inserted from the endoscope entry port 112. The insertion part 12 inserted in the endoscope entry port 112 is delivered from the endoscope exit port 116 through the outer tube body 102. At this time, the insertion part 12 is delivered from the endoscope exit port 116 through the endoscope holding hole 132 formed in the slider 118 in the outer tube body. The O-ring 134 is included in the endoscope holding hole 132, and the insertion part 12 passing through the endoscope holding hole 132 is held to the slider 118 by the elastic force of the O-rings 134.

Next, the insertion part 52 of the treatment tool 50 is inserted from the treatment tool entry port 108. The insertion part 52 inserted in the treatment tool entry port 108 is delivered from the treatment tool exit port 114 through the outer tube body 102. At this time, the insertion part 52 is held to the sleeve 140 by the elastic force of the O-rings 130.

Figure 9:
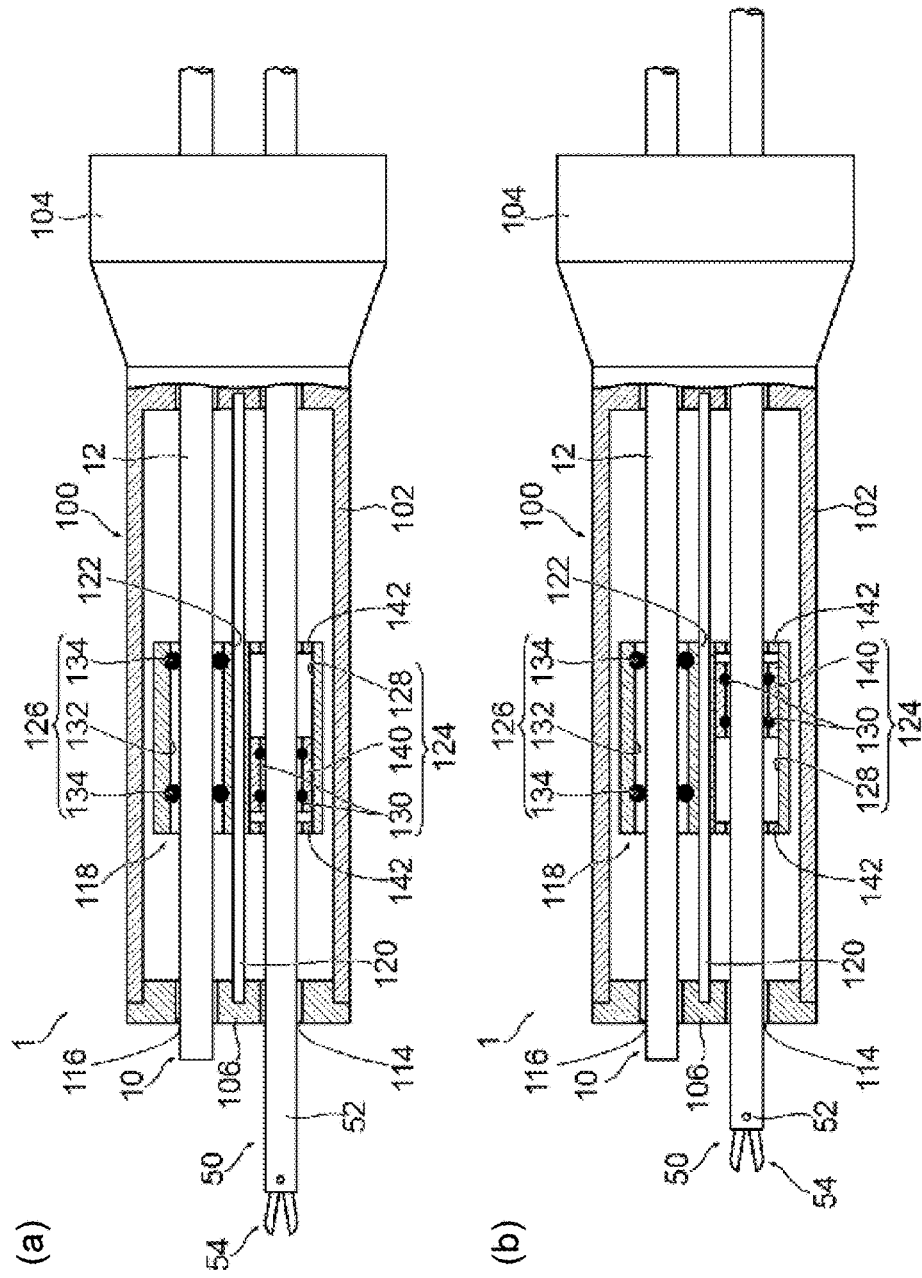
FIG. 9 is an explanatory diagram illustrating a mode when an endoscopic surgery device is used, in which an insertion part of the treatment tool is moved in an axial direction of the outer tube from a state illustrated in portion (a) to a state illustrated in portion (b).

FIG. 9 is a diagram illustrating a mode when the endoscopic surgery device 1 is used. In FIG. 9, the insertion part 52 of the treatment tool 50 is moved in an axial direction of the outer tube 100 from a state illustrated in portion (a) to a state illustrated in portion (b).

The insertion part 12 of the endoscope 10 and the insertion part 52 of the treatment tool 50, which are inserted in the outer tube 100, are held in parallel to each other and held in parallel to the axis of the outer tube 100.

Here, the insertion part 52 of the treatment tool 50 is held to the sleeve 140, and the sleeve 140 is provided so as to be movable in the axial direction with respect to the slider 118. Further, the friction force (F3) between the sleeve 140 and the treatment tool holding hole 128 and the friction force (F1) between the guide shafts 120 and the guide holes 122 are set to F3<F1.

As a result of this, when the insertion part 52 of the treatment tool 50 is moved in the axial direction, only the treatment tool 50 moves in the range of the movable amount (allowance amount) of the sleeve 140 defined by the pair of stopper rings 142 and 142.

On the other hand, when the insertion part 52 of the treatment tool 50 is moved in the axial direction over the range of the movable amount of this sleeve 140, the slider 118 is pressed by the sleeve 140 and moves in an integral manner with the treatment tool 50. As a result of this, the insertion part 12 of the endoscope 10 moves in interlock with the treatment tool 50.

Specifically, when the insertion part 52 of the treatment tool 50 is moved in the distal end direction over the range of the movable amount of the sleeve 140, the distal end of the sleeve 140 abuts on the stopper ring 142 provided in the end part on the distal end side of the treatment tool holding hole 128, and this slider 118 moves in the distal end direction in an integral manner with the treatment tool 50. As a result of this, the insertion part 12 of the endoscope 10 moves in the distal end direction together with the treatment tool 50.

On the other hand, when the insertion part 52 of the treatment tool 50 is moved in the proximal end direction, the proximal end of the sleeve 140 abuts on the stopper ring 142 provided in the end part on the proximal end side of the treatment tool holding hole 128, and this slider 118 moves in the proximal end direction in an integral manner with the treatment tool 50. As a result of this, the insertion part 12 of the endoscope 10 moves in the proximal end direction together with the treatment tool 50.

Thus, according to the endoscopic surgery device 1, it is possible to move the endoscope 10 in interlock with the treatment tool 50 only when the treatment tool 50 is greatly moved. By this means, regarding the movement of small amplitude like minute shake, since the movement is not transmitted to the endoscope 10, it is possible to provide an excellent endoscopic image without shake.

<<Usage Example of Endoscopic Surgery Device 1>>

Figure 10:
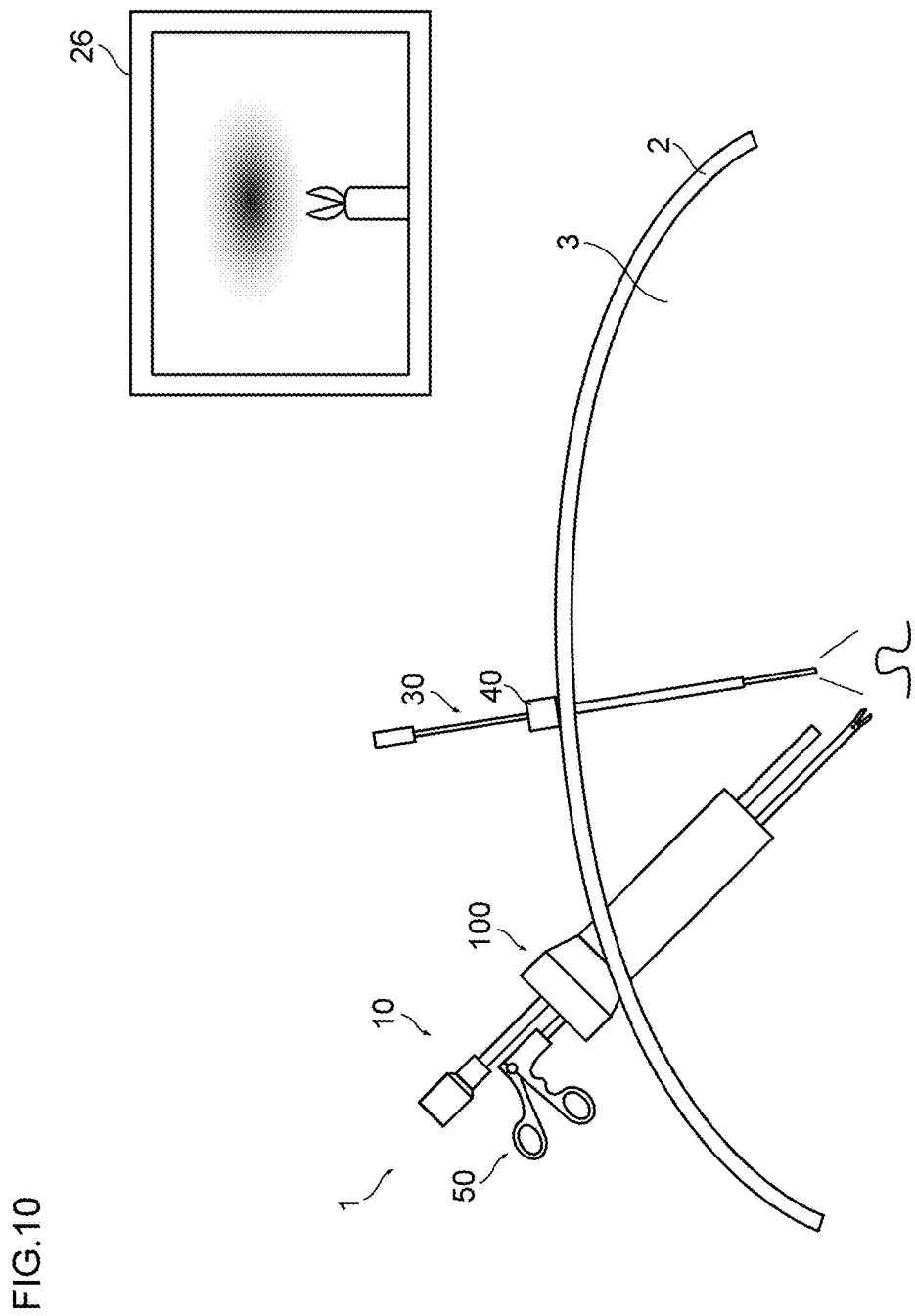
FIG. 10 is a schematic explanatory diagram illustrating one example of a surgery procedure using an endoscopic surgery device.

FIG. 10 is a schematic diagram illustrating one example of a surgery procedure using the endoscopic surgery device 1.

This example shows an example in a case where one surgeon performs treatment.

The endoscope 10 and the treatment tool 50 are inserted in a body cavity 3 through the outer tube 100 tapped into a body cavity wall 2 of the patient. The endoscope 10 moves in interlock with the movement of the treatment tool 50. By this means, an image of a site to be treated is always displayed on the display 26, and the visual field can be moved by the movement of the treatment tool 50.

Since illumination means is not included in the endoscope 10, the needle light 30 is separately inserted in the body cavity 3 through the trocar 40 for the needle light, as illumination means. The body cavity 3 is illuminated by illumination light emitted from the distal end of the needle light 30. Here, one piece of the needle light 30 is exemplified in this example, but multiple pieces of the needle light 30 may be used according to the necessity. As mentioned above, since the endoscope 10 is also operated by the operation of the treatment tool 50, a scopist becomes unnecessary.

<<Configuration of Valve Member 160 of Outer Tube 100>>

Figure 11:
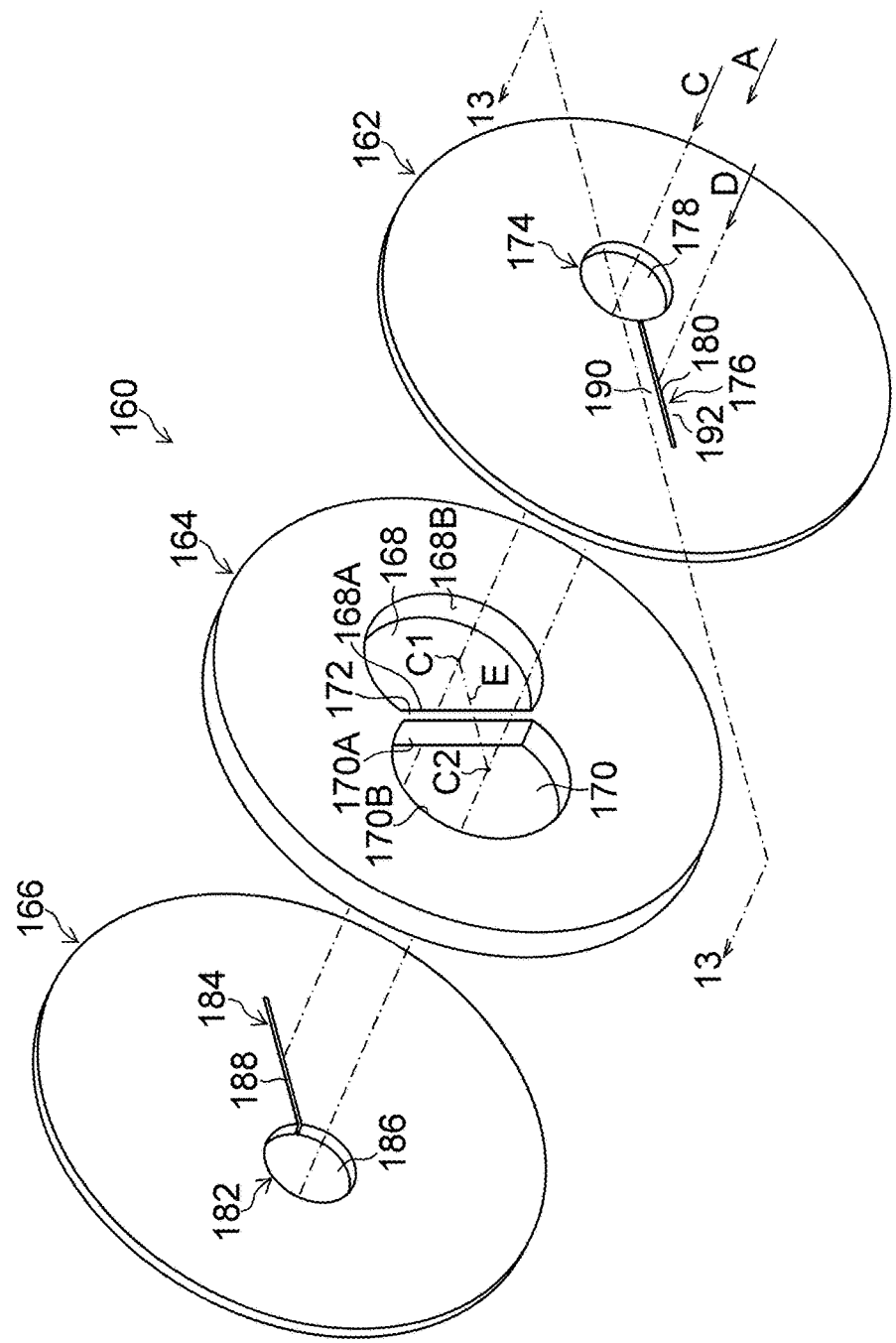
FIG. 11 is an assembly perspective view of a valve member of an embodiment.
Figure 12:
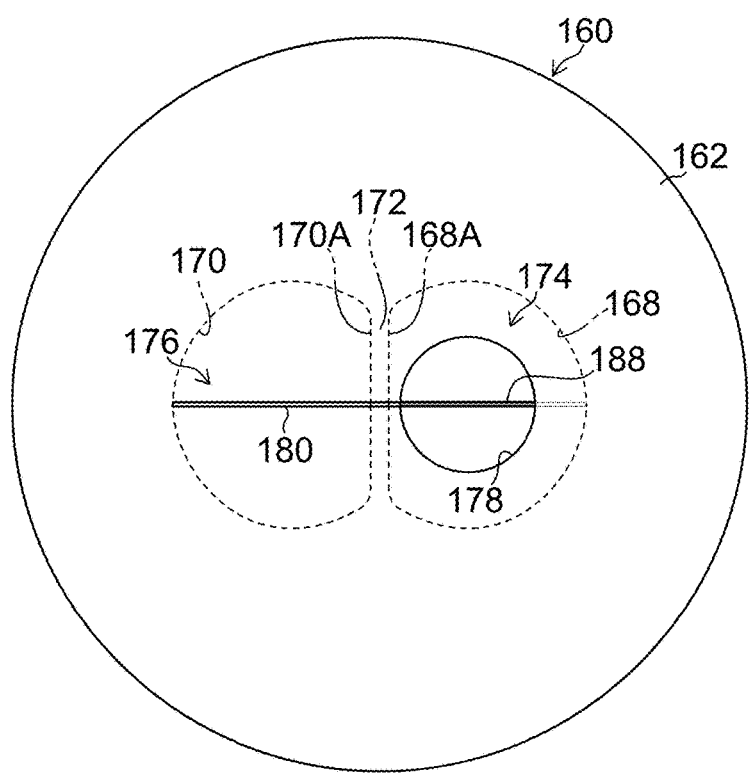
FIG. 12 is a front view in which the valve member in FIG. 11 is seen from the direction of arrow A.
Figure 13:
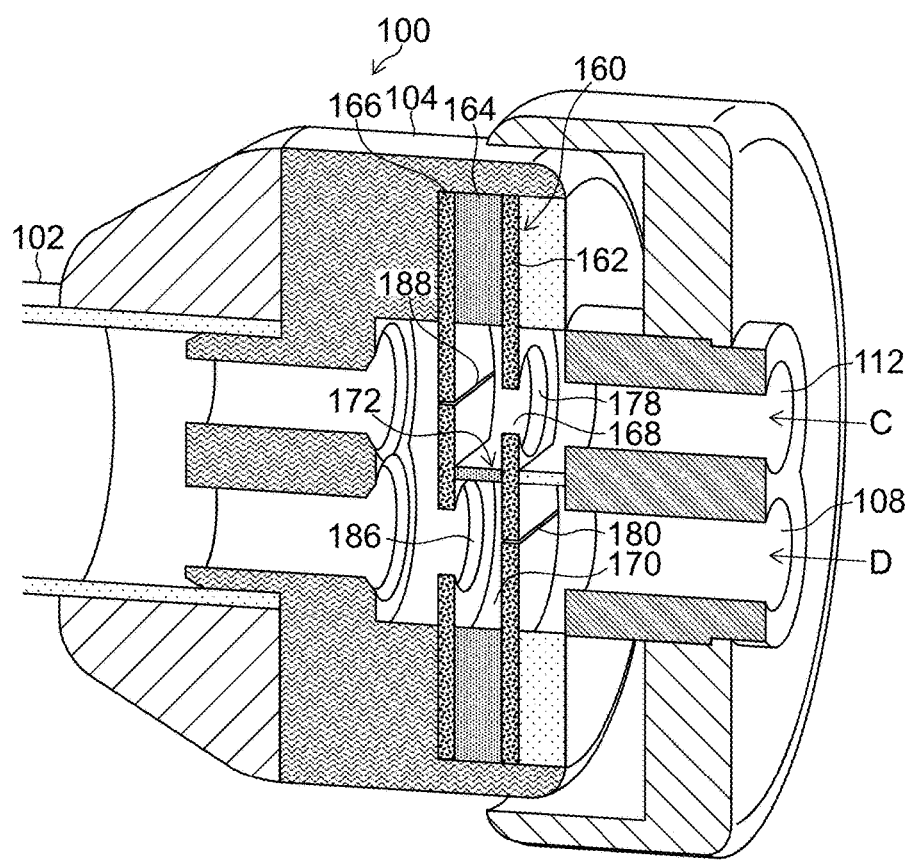
FIG. 13 is a cross-sectional view along line 13-13 in FIG. 11 in a mode in which a valve member is disposed in a cap.

FIG. 11 is an assembly perspective view of the valve member 160 of an embodiment, FIG. 12 is a front view in which the valve member 160 in FIG. 11 is seen from the direction of arrow A, and FIG. 13 is a cross-sectional view along line 13-13 in FIG. 11 in a mode in which the valve member 160 is disposed in the cap 104.

The valve member 160 is configured by arranging a valve body 162, an intermediate member (insertion member) 164 and a valve body 166 in parallel from the proximal end of the cap 104 to the distal end.

As illustrated in FIG. 11, the valve body 162, the intermediate member 164 and the valve body 166 are disc-shaped members having the same diameter, and they are disposed in a predetermined position in the cap 104 illustrated in FIG. 13 in a state where they are stacked so as to allow their centers to be matched.

Moreover, it is preferable that the valve body 162, the intermediate member 164 and the valve body 166 are integrated by a bonding agent applied to each peripheral part or an engagement tool (not illustrated) which penetrates each engagement hole (not illustrated), and they are formed as a unit valve body.

The valve bodies 162 and 166 in FIG. 11 include elastic members such as natural rubber, synthetic rubber and silicone rubber, and have a function to secure the airtightness of the outer tube 100. The intermediate member 164 is made of metal such as stainless steel and aluminum or made of rigid plastic, and has a function to reinforce the valve bodies 162 and 166 overlapped back and forth.

Moreover, two insertion holes of an insertion hole (first insertion hole) 168 and an insertion hole (second insertion hole) 170 which have the same shape as each other are adjacently provided in the intermediate member 164.

The insertion part 12 (first insertion part) of the endoscope 10 is inserted in the insertion hole 168 from the endoscope entry port 112 in FIG. 13 to the direction of arrow C in FIG. 11, and the insertion part 12 is moved back and forth with respect to the insertion hole 168 at the time of operation. Moreover, the insertion part 52 (second insertion part) of the treatment tool 50 is inserted in the insertion hole 170 from the treatment tool entry port 108 in FIG. 13 to the direction of arrow D in FIG. 11, and the insertion part 52 is moved back and forth with respect to the insertion hole 170 at the time of operation.

In addition, the insertion holes 168 and 170 which are formed in a D-shape are disposed via a tabular partition wall 172 provided in the central part in a surface orthogonal to respective axial directions (which are the same directions as the directions of arrows C and D and parallel to the axis of the outer tube body 102) of the insertion holes 168 and 170. That is, D-shaped cut parts 168A and 170A of the insertion holes 168 and 170 are formed by the partition wall 172, and the insertion holes 168 and 170 are disposed in the intermediate member 164 such that the D-shaped cut parts 168A and 170A face each other. That is, the insertion holes 168 and 170 are included in line-symmetrical positions with respect to the partition wall 172.

The valve body 162 is a valve body in which an opening type airtight valve (first opening type airtight valve) 174 and a slit type airtight valve (second slit type airtight valve) 176 are integrated.

A circular opening 178 (first opening) is provided in the opening type airtight valve 174. The opening 178 is disposed on the same axis as the insertion hole 168 and formed to be slightly smaller than the external diameter of the insertion part 12 of the endoscope 10. Therefore, when the insertion part 12 is internally fitted to the opening 178, the inner peripheral edge of the opening 178 closely contacts with the outer peripheral surface of the insertion part 12. Therefore, the airtightness of the endoscope entry port 112 is maintained.

The slit type airtight valve 176 is provided with a slit (second slit) 180. This slit 180 is formed in a position overlapping with the insertion hole 170 as seen from the insertion direction of the insertion part 52 of the treatment tool 50 shown by the direction of arrow D. When the insertion part 52 is removed from the treatment tool entry port 108, this slit 180 closes. Therefore, the airtightness of the treatment tool entry port 108 is maintained.

Similarly, the valve body 166 is a valve body in which an opening type airtight valve (second opening type airtight valve) 182 and a slit type airtight valve (first slit type airtight valve) 184 are integrated.

A circular opening (second opening) 186 is provided in the opening type airtight valve 182. The opening 186 is disposed on the same axis as the insertion hole 170 and formed to be slightly smaller than the external diameter of the insertion part 52 of the treatment tool 50. Therefore, when the insertion part 52 is internally fitted to the opening 186, the inner peripheral edge of the opening 186 closely contacts with the outer peripheral surface of the insertion part 52. Therefore, the airtightness of the treatment tool entry port 108 is maintained.

The slit type airtight valve 184 is provided with a slit (first slit) 188. This slit 188 is formed in a position overlapping with the insertion hole 168 as seen from the insertion direction of the insertion part 12 of the endoscope 10 shown by the direction of arrow C. When the insertion part 12 is removed from the endoscope entry port 112, this slit 188 closes. Therefore, the airtightness of the endoscope entry port 112 is maintained.

As mentioned above, the valve member 160 of the embodiment can secure the airtightness by the openings 178 and 186 when the insertion parts 12 and 52 are inserted, and the valve member 160 can secure the airtightness by the slits 180 and 188 when the insertion parts 12 and 52 are removed.

Moreover, since the slit type airtight valve 176 and the slit type airtight valve 184 are disposed in mutually shifted positions in the axial direction of the longitudinal axis of the outer tube body 102, for example, the opening and closing operation of the slit type airtight valve 176 does not influence the opening and closing operation of the slit type airtight valve 184. That is, in a case where the slit type airtight valve 176 and the slit type airtight valve 184 are integrally formed, there is a case where the opening and closing operation of the slit type airtight valve 176 influences the opening and closing operation of the slit type airtight valve 184. However, since the slit type airtight valves 176 and 184 are formed in the separate valve bodies 162 and 166 respectively in the present embodiment, such a problem does not occur.

By the way, the slits 180 and 188 are disposed along reference line E connecting centers C1 and C2 of respective arcs of the insertion holes 168 and 170 as seen from the axial directions of the insertion holes 168 and 170. Moreover, the insertion holes 168 and 170 are formed in a line-symmetric shape with respect to the reference line E.

<<Features of Outer Tube 100 of Embodiment>> a) First Feature

When the slit type airtight valves 176 and 184 are projected on a surface orthogonal to the insertion holes 170 and 168, they are formed in a line-symmetric shape centering on reference line E. Moreover, when the insertion holes 168 and 170 are projected on a surface orthogonal to the insertion holes 170 and 168, they are formed in a line-symmetric shape centering on reference line E. Further, two insertion holes 168 and 170 are formed in a cross-sectional D-shape and disposed via the partition wall 172. That is, the insertion holes 168 and 170 are formed with the arc part and the straight line part, and, for example, the distance between the centers of the arcs of the insertion holes 168 and 170 (the distance between C1 and C2) is made shorter than the distance between the centers in a case where the insertion holes 168 and 170 are complete circles. By this means, it is possible to decrease the external diameter of the outer tube body 102. It is specifically described below.

Figure 14:
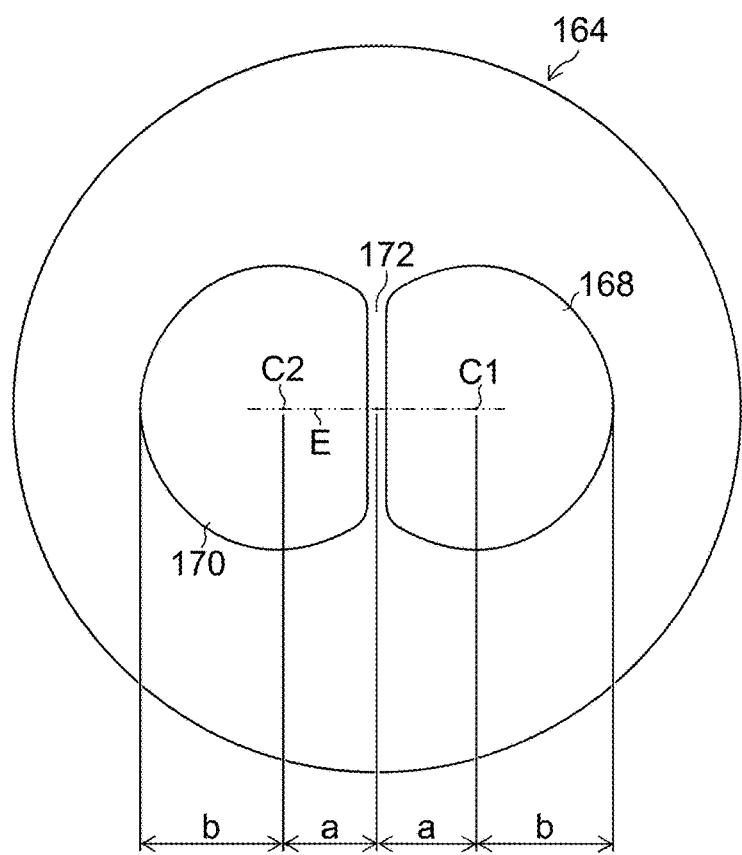
FIG. 14 is a front view of an intermediate member.

FIG. 14 is a front view of the intermediate member 164.

The insertion holes 168 and 170 have a line-symmetric shape centering on the reference line E that passes through the center C1 of the arc of the insertion hole 168 and the center C2 of the arc of the insertion hole 170. Moreover, on the reference line E in the insertion hole 168, the distance "a" from the center C1 of the insertion hole 168 to the wall core of the partition wall 172 is shorter than distance "b" from the center C1 to the edge part of the arc part on the side opposite to the partition wall 172. Similarly, also in the insertion hole 170, on the reference line E, the distance "a" from the center C2 of the insertion hole 170 to the wall core of the partition wall 172 is shorter than distance "b" from center C2 to the edge part of the arc part on the side opposite to the partition wall 172. By this means, since the distance between the centers of the insertion hole 168 and the insertion hole 170 (the distance between C1 and C2) is shorter than the distance between the centers in a case where the insertion holes 168 and 170 are complete circles, it is possible to decrease the external diameter of the outer tube body 102.

b) Second Feature

The opening type airtight valve 174 and the slit type airtight valve 184 are disposed so as to interpose the insertion hole 168 therebetween, and the slit type airtight valve 176 and the opening type airtight valve 182 are provided so as to interpose the insertion hole 170 therebetween.

Regarding the insertion hole 168, since the slit 188 of the slit type airtight valve 184 closes when the insertion part 12 of the endoscope 10 is removed, it is possible to secure the airtightness of the insertion hole 168. Moreover, regarding the insertion hole 168, since the insertion part 12 is internally fitted to the opening 178 of the opening type airtight valve 174 when the insertion part 12 is inserted, that is, since the inner peripheral edge of the opening 178 closely contacts with the outer peripheral surface of the insertion part 12, it is possible to secure the airtightness of the insertion hole 168.

On the other hand, regarding the insertion hole 170, since the slit 180 of the slit type airtight valve 176 closes when the insertion part 52 of the treatment tool 50 is removed, it is possible to secure the airtightness of the insertion hole 170. Moreover, regarding the insertion hole 170, since the insertion part 52 is internally fitted to the opening 186 of the opening type airtight valve 182 when the insertion part 52 is inserted, that is, since the inner peripheral edge of the opening 186 closely contacts with the outer peripheral surface of the insertion part 52, it is possible to secure the airtightness of the insertion hole 170.

c) Third Feature

Taking into account the first feature, the slits 180 and 188 are disposed along the reference line E in a surface orthogonal to the insertion holes 170 and 168.

In this embodiment, two leaflets 190 and 192 on both sides of the slit 180 illustrated in FIG. 13 abut on an arc edge 170B of the insertion hole 170 and a D-shaped cut part 170A of the partition wall 172 respectively when the insertion part 52 of the treatment tool 50 is internally fitted, and are deformed into the same shape.

Therefore, since there is no difference in stress caused in the two leaflets 190 and 192, it is possible to secure the airtightness by the slit 180 over a long period of time. Moreover, since two leaflets 190 and 192 are deformed into the same shape, they smoothly return to the original shapes when the insertion part 52 is removed.

Here, in the embodiment, the slits 180 and 188 are disposed along the reference line E, that is, they are disposed on the reference line E, but the arrangement is not limited to this.

That is, the slits 180 and 188 only have to be disposed in a nonparallel state with respect to the partition wall 172 as seen from the axial directions of the insertion holes 168 and 170. As one example, the slits 180 and 188 may be disposed along a direction vertical to the partition wall 172 as seen from the axial directions of the insertion holes 168 and 170. That is, an arrangement of the slits 180 and 188 may be acceptable as long as the slits 180 and 188 are not disposed in parallel to the partition wall 172.

By this means, as compared with the valve member in PTL 2 in which a slit is formed in parallel to a partition wall, it is possible to make the deformed shapes of two leaflets 190 and 192 close to the same shape when the insertion part 52 is internally fitted. Therefore, since it is possible to reduce a difference in stress caused in two leaflets 190 and 192, it is possible to secure the airtightness by the slit 180 over a long period of time.

d) Fourth Feature

The valve member 160 formed with the valve body 162, the intermediate member 164 and the valve body 166 is housed in the cap 104 of the proximal end of the outer tube body 102. By this means, it is possible to install the valve member 160 in the outer tube 100 without increasing the external diameter of the outer tube body 102, that is, without influencing invasion added to a body wall.

e) Fifth Feature

The valve member 160 formed with the valve body 162, the intermediate member 164 and the valve body 166 is configured as an integrated unit valve body. By assuming the valve member 160 as a unit valve body, the assemblability of the valve member 160 to the outer tube 100 improves, and the handling of storage and management, and so on, of the valve member 160 becomes easy.

f) Sixth Feature

The opening 178 is set to be an insertion opening of the insertion part 12 of the endoscope 10, and the opening 186 is set to be an insertion opening of the insertion part 52 of the treatment tool 50. By this means, since the endoscope 10 and the treatment tool 50 can be inserted in the outer tube 100, it is possible to operate the endoscope 10 by a surgeon who operates the treatment tool 50. Therefore, since a scopist who operates the endoscope 10 becomes unnecessary, it is possible to solve a problem that surgeon's hands and scopist's hands interfere with each other above patient's abdominal wall. Further, since the work space of the surgeon becomes wide, the surgery operability improves.

In this embodiment, it is preferable that the diameter of the opening 178 is larger than the diameter of the opening 186. It is because, since an optical system including multiple lenses and a built-in element such as a signal cable are inserted in the insertion part 12 of the endoscope 10, the external diameter of the insertion part 12 is generally larger than the external diameter of the insertion part 52 of the treatment tool 50. Here, if the openings 178 and 186 and the slits 180 and 188 are configured to have the same shapes as each other, it is possible to share the valve bodies 162 and 166.

g) Seventh Feature

The opening type airtight valve 174 and the slit type airtight valve 176 are integrally configured, and the opening type airtight valve 182 and the slit type airtight valve 184 are integrally configured. That is, since the opening type airtight valve 174 and the slit type airtight valve 176 are integrated and the opening type airtight valve 182 and the slit type airtight valve 184 are integrated, it is possible to reduce the number of parts of the valve member 160. Moreover, the assembly of the valve member 160 to the outer tube 100 improves, and the handling of storage and management, and so on, of the valve member 160 becomes also easy.

<Another Embodiment of Valve Member>

Figure 15:
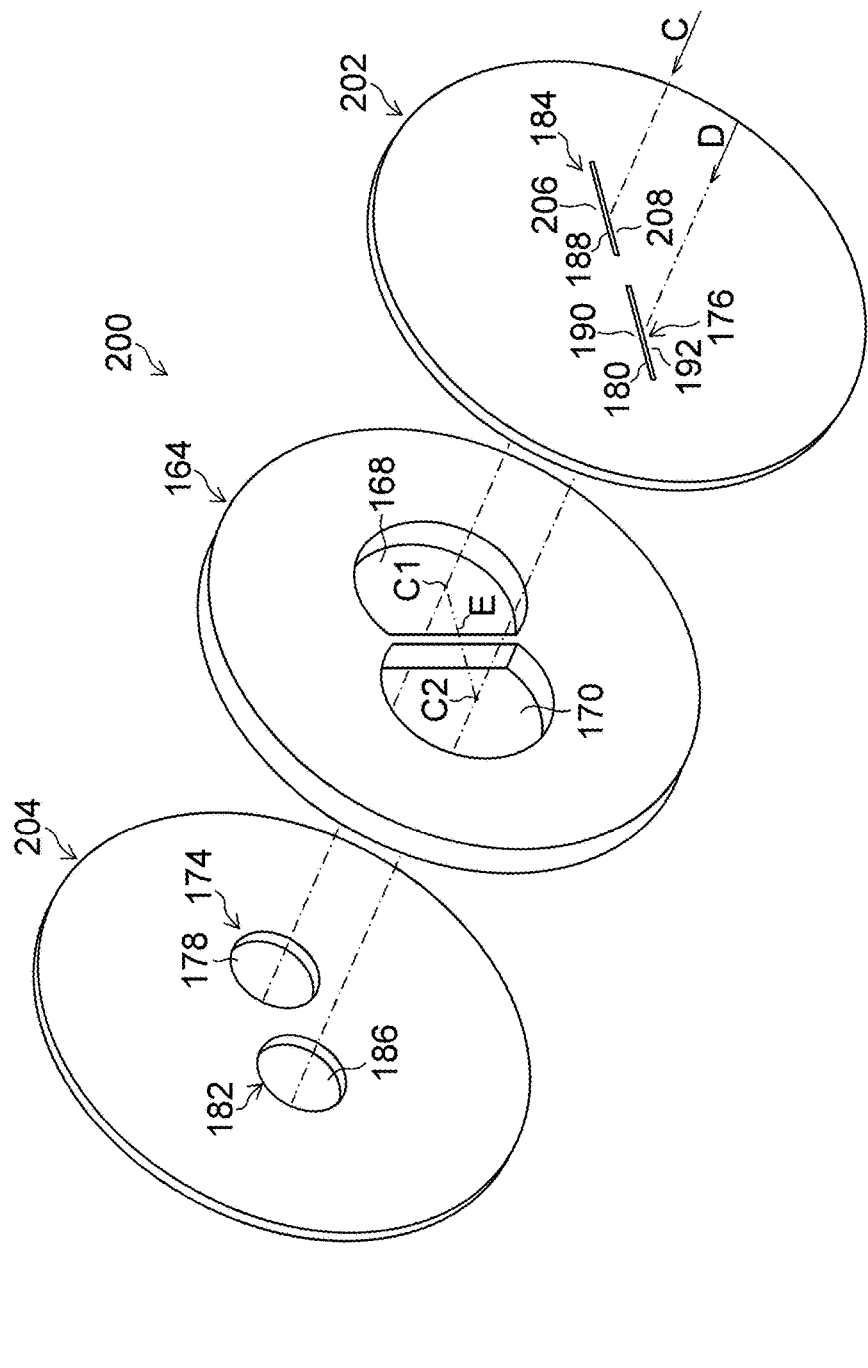
FIG. 15 is an assembly perspective view illustrating another embodiment of a valve member.

A valve member 200 of another embodiment illustrated in FIG. 15 includes valve bodies 202 and 204 and the intermediate member 164. In the valve member 200, the slit type airtight valves 176 and 184 are integrally configured as the valve body 202, and the opening type airtight valves 174 and 182 are integrally configured as the valve body 204. The valve body 202 is disposed on the proximal end side with respect to the intermediate member 164, and the valve body 204 is disposed on the distal end side with respect to the intermediate member 164.

In the valve member 200 in this embodiment, the slits 180 and 188 are provided in one valve body 202 disposed on the proximal end side, and the slits 180 and 188 are disposed along the reference line E. By this means, two leaflets 190 and 192 on both sides of the slit 180 are deformed into the same shape with respect to the insertion hole 170, and two leaflets 206 and 208 on both sides of the slit 188 are deformed into the same shape with respect to the insertion hole 168.

Figure 16:
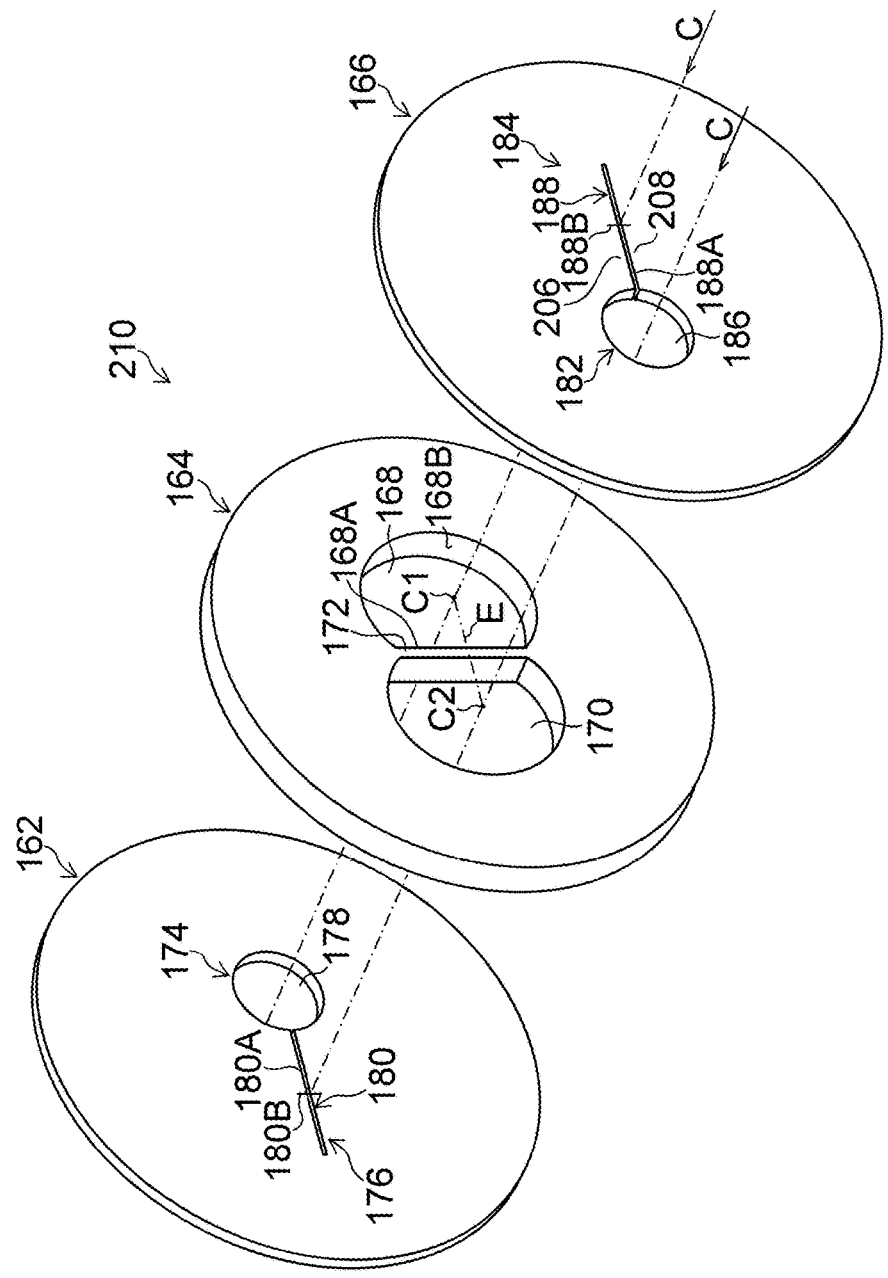
FIG. 16 is an assembly perspective view illustrating another embodiment of a valve member.

A valve member 210 of another embodiment illustrated in FIG. 16 includes the valve bodies 162 and 166 and the intermediate member 164. In the valve member 210, the valve body 162 is disposed on the distal end side with respect to the intermediate member 164, and the valve body 166 is disposed on the proximal end side with respect to the intermediate member 164.

In this embodiment, the slit 188 is disposed along the reference line E connecting respective centers C1 and C2 of the insertion holes 168 and 170 as seen from the axial directions of the insertion holes 168 and 170. Therefore, two leaflets 206 and 208 on both sides of the slit 188 abut on an arc edge 168B of the insertion hole 168 and a D-shaped cut part 168A of the partition wall 172 respectively when the insertion part 12 of the endoscope 10 is internally fitted, and they are deformed into the same shape. Therefore, since there is no difference in stress caused in two leaflets 206 and 208, it is possible to secure the airtightness by the slit 188 over a long period of time. Moreover, since two leaflets 206 and 208 are deformed into the same shape, they smoothly return to the original shapes when the insertion part 12 is removed.

Moreover, the slits 180 and 188 are formed in a cross shape in the valve member 210. The shapes of the slits 180 and 188 of the embodiment is configured to have a straight-line shape as reference, but, in a case where they have a cross shape like FIG. 16, the longer slits 180A and 188A among two slits 180A and 180B and two slits 188A and 188B forming the cross-shaped slits 180 and 188 function as the slits 180 and 188 of the first embodiment.

Figure 17:
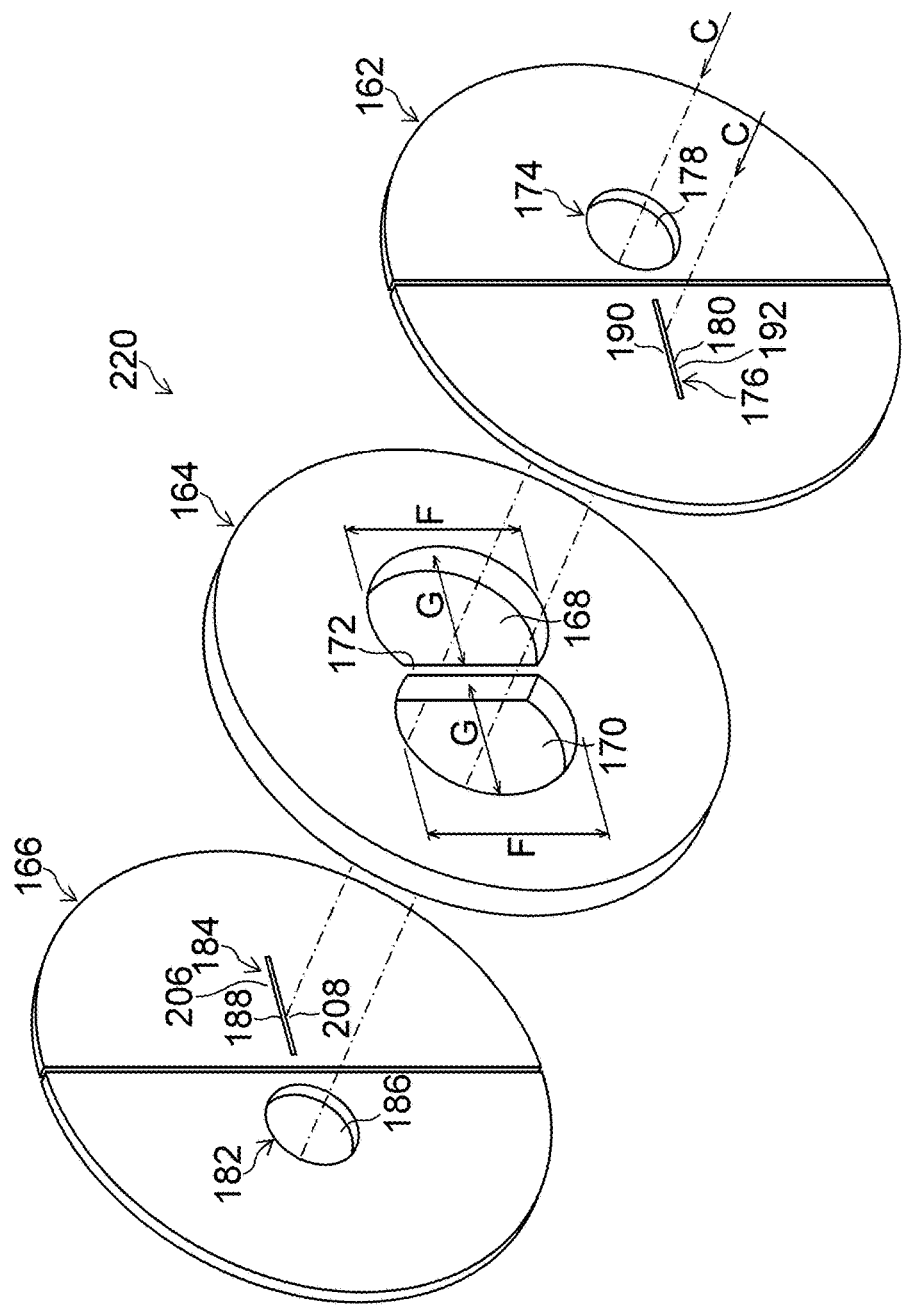
FIG. 17 is an assembly perspective view illustrating another embodiment of a valve member.

In a valve member 220 of another embodiment illustrated in FIG. 17, as for the valve member 160 illustrated in FIG. 11, the opening type airtight valve 174 and the slit type airtight valve 176 which form the valve body 162 are separately formed, and the opening type airtight valve 182 and the slit type airtight valve 184 which form the valve body 166 are separately formed.

In the valve member 220 in this embodiment, the number of parts increases as compared with the valve member 160 illustrated in FIG. 11, but an operational effect similar to the valve member 160 illustrated in FIG. 11 is obtained. Here, the shape of each valve is not limited to a semicircular shape, and it may be a circular shape or a rectangular shape.

Moreover, the insertion holes 168 and 170, each of which has a major axis F and a minor axis G in a cross-section orthogonal to the longitudinal axis of the outer tube body 102. The slits 180 and 188 of the slit type airtight valves 176 and 184 are formed along the minor axis G.

By this means, respective leaflets 190, 192, 206 and 208 forming the slits 180 and 188 are elastically deformed into the direction of the major axis F of the insertion holes 168 and 170. Since the elastic deformation amounts of the leaflets 190, 192, 206 and 208 are less restricted in the direction of the major axis F compared to the direction of the minor axis G, the load (stress) at elastic deformation is mitigated in a case where the leaflets 190, 192, 206 and 208 are elastically deformed into the direction of the major axis F as compared with a case where the leaflets 190, 192, 206 and 208 are elastically deformed into the direction of the minor axis G. Therefore, the service life of the slit type airtight valves 176 and 184 is prolonged.

Figure 18:
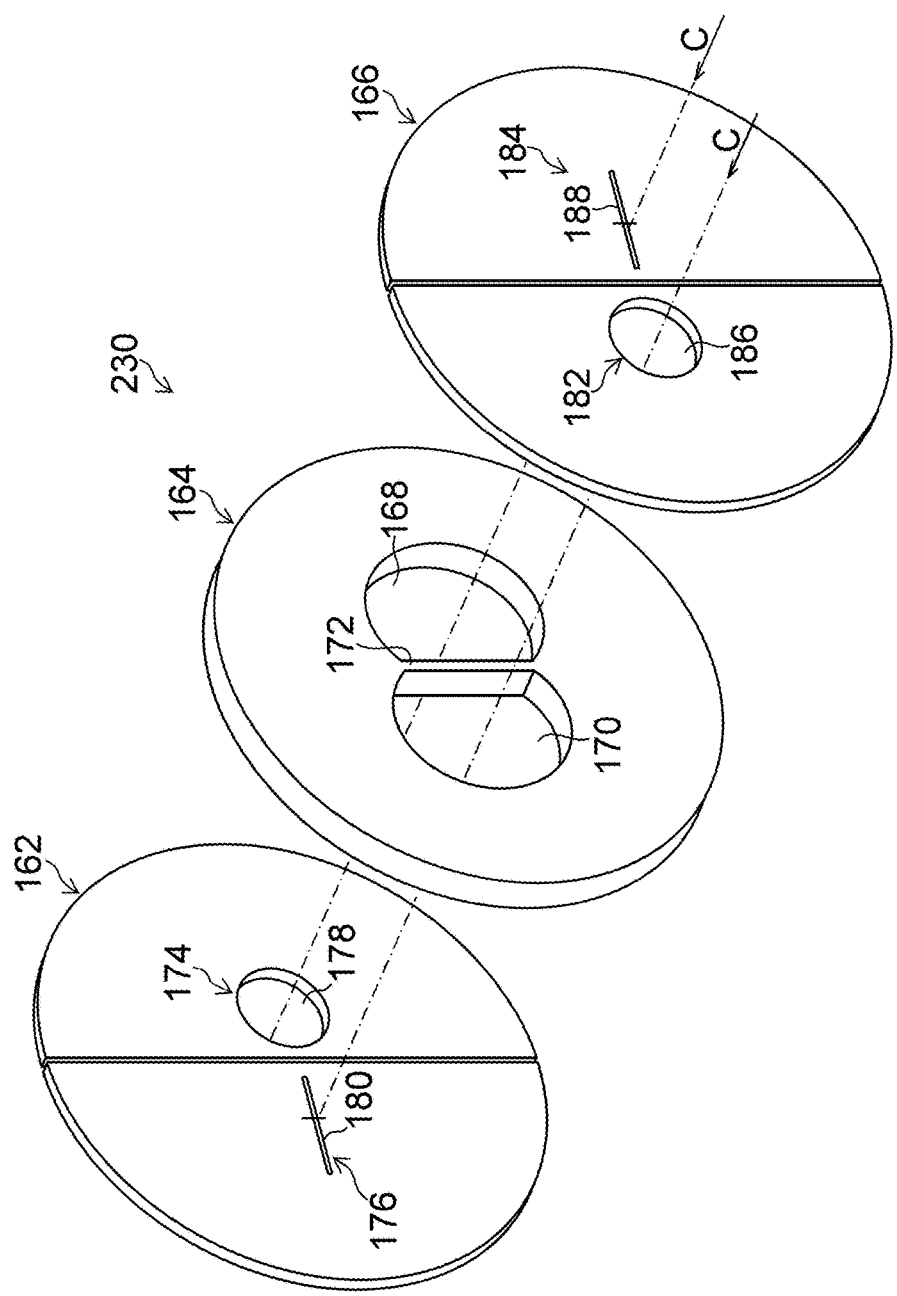
FIG. 18 is an assembly perspective view illustrating another embodiment of a valve member.

In a valve member 230 of another embodiment illustrated in FIG. 18, as for the valve member 210 illustrated in FIG. 16, the opening type airtight valve 182 and the slit type airtight valve 184 which form the valve body 166 are separately formed, and the opening type airtight valve 174 and the slit type airtight valve 176 which form the valve body 162 are separately formed.

In the valve member 230 in this embodiment, the number of parts increases as compared with the valve member 210 illustrated in FIG. 16, but an operational effect similar to the valve member 210 illustrated in FIG. 16 is obtained.

Figure 19:
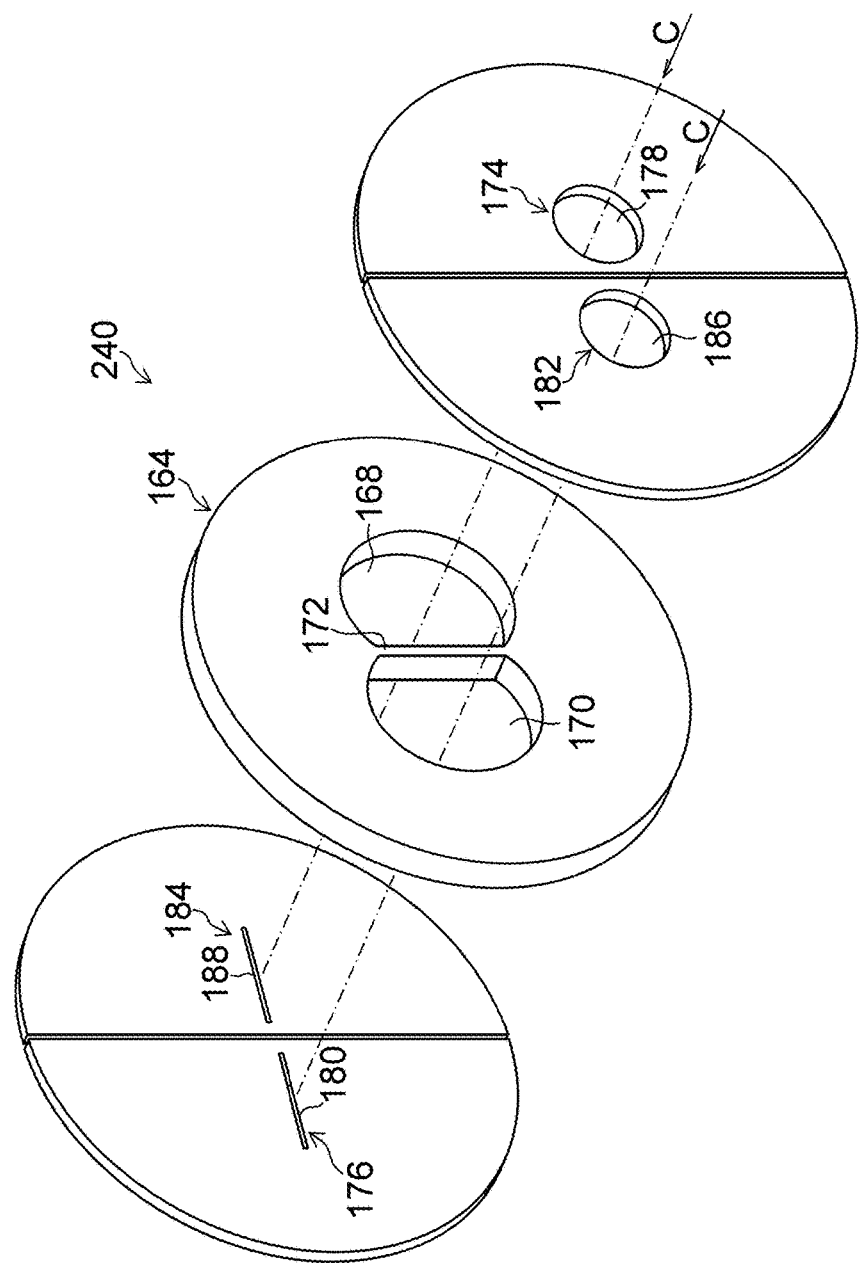
FIG. 19 is an assembly perspective view illustrating another embodiment of a valve member.

In a valve member 240 of another embodiment illustrated in FIG. 19, as compared with the valve member 220 illustrated in FIG. 17, the slit type airtight valve 176 is disposed on the distal end side with respect to the intermediate member 164 and the opening type airtight valve 182 is disposed on the proximal end side with respect to the intermediate member 164.

Figure 20:
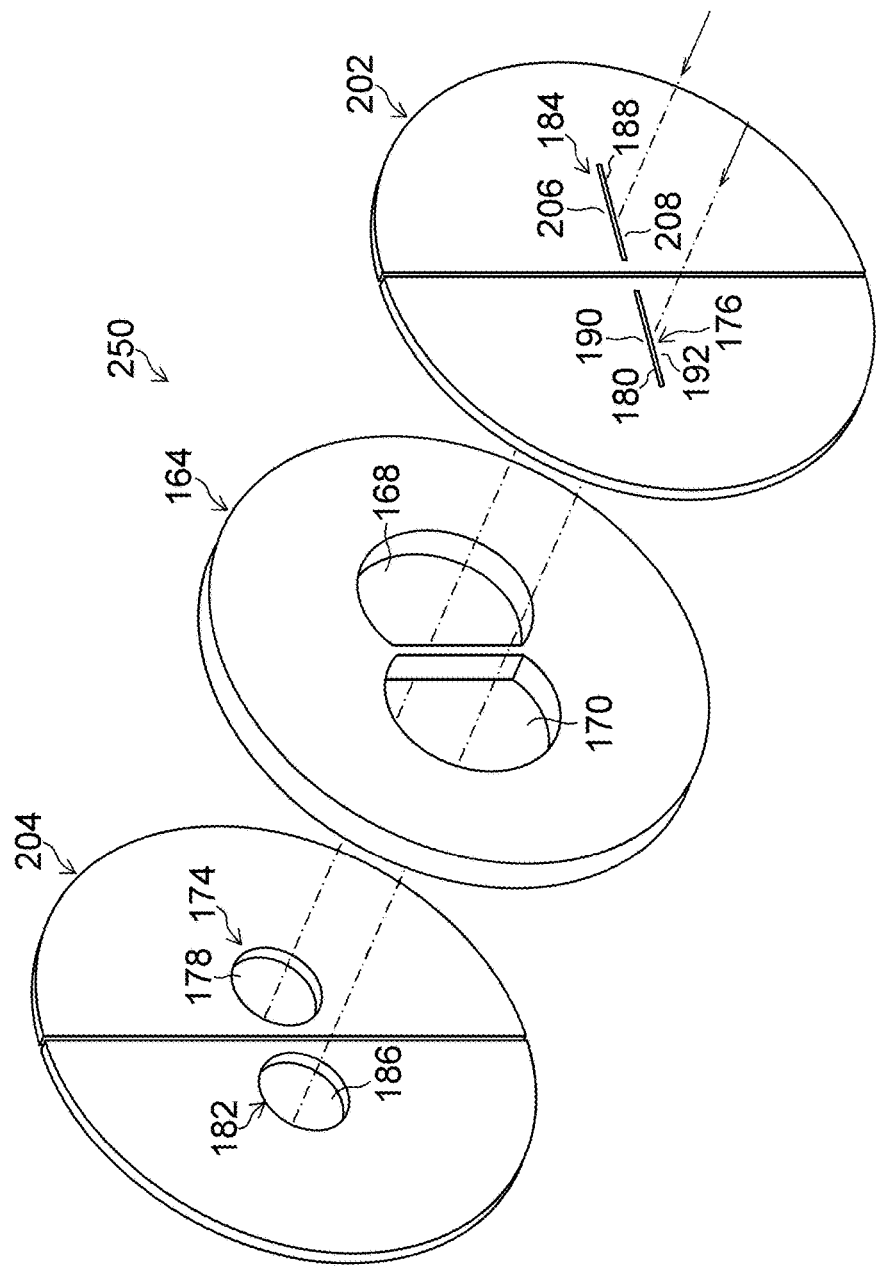
FIG. 20 is an assembly perspective view illustrating another embodiment of a valve member.

In a valve member 250 of another embodiment illustrated in FIG. 20, as compared with the valve member 200 illustrated in FIG. 15, the valve body 202 is divided into the slit type airtight valve 176 and the slit type airtight valve 184, and the valve body 204 is divided into the opening type airtight valve 174 and the opening type airtight valve 182.

In the valve member 250 in this embodiment, the number of parts increases as compared with the valve member 200 illustrated in FIG. 15, but an operational effect similar to the valve member 200 illustrated in FIG. 15 is obtained.

Figure 21:
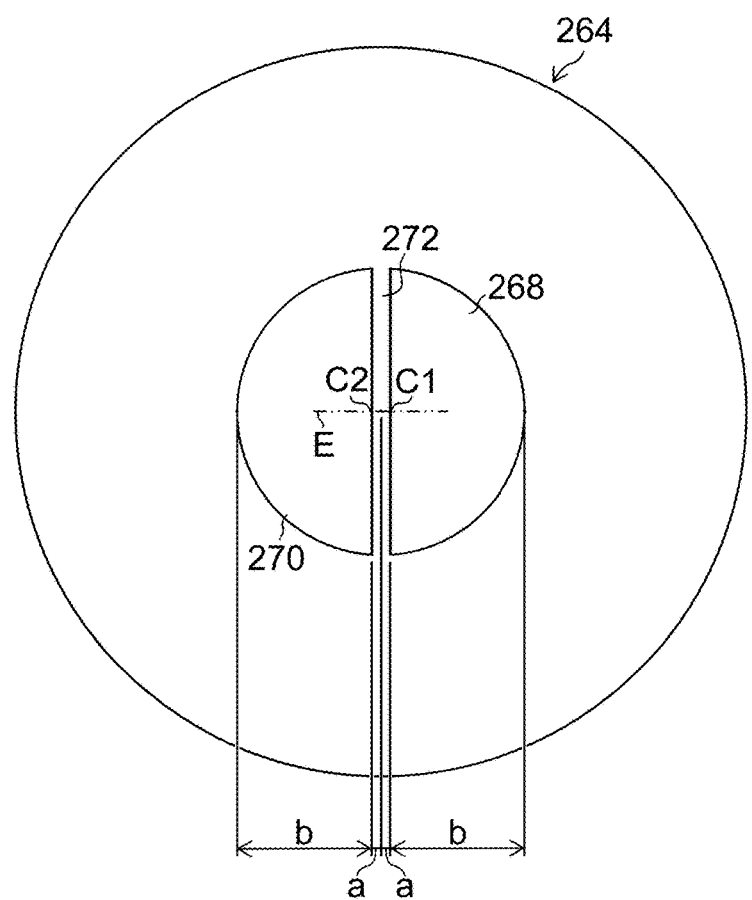
FIG. 21 is a front view illustrating another embodiment of an intermediate member.

FIG. 21 is a front view illustrating another modification example of an intermediate member 264.

The intermediate member 264 includes semicircular insertion holes 268 and 270 disposed via a tabular partition wall 272. That is, the insertion holes 268 and 270 have a line-symmetric shape centering on the reference line E that pass through the center C1 of the arc of the insertion hole 268 and the center C2 of the arc of the insertion hole 270. Moreover, on the reference line E in the insertion hole 268, a distance "a" from the center C1 of the insertion hole 268 to the wall core of the partition wall 272 is shorter than a distance "b" from the center C1 to the edge part of the arc part on the side opposite to the partition wall 272. Similarly, also in the insertion hole 270, on the reference line E, a distance "a" from the center C2 of the insertion hole 270 to the wall core of the partition wall 272 is shorter than a distance "b" from the center C1 to the edge part of the arc part on the side opposite to the partition wall 272. By this means, since the distance between the centers of the insertion hole 268 and the insertion hole 270 (the distance between C1 and C2) is shorter than the distance between the centers in a case where the insertion holes 268 and 270 are complete circles, it is possible to decrease the external diameter of the outer tube.

Here, the D-shaped insertion holes 168 and 170 and the semicircular insertion holes 268 and 270 are exemplified as a shape of an insertion hole in the embodiments, but they are not limited to these, and any shape is acceptable without departing from the spirit of the present invention.

<Appendix>

An outer tube comprising:

a penetration part configured to include a distal end, a proximal end and a longitudinal axis, and to penetrate a body wall;

a first insertion hole in which a first insertion part of one of two medical instruments to be inserted inside the penetration part can be inserted in the inside of the penetration part along a direction parallel to the longitudinal axis so as to be freely movable back and forth;

a second insertion hole which is disposed adjacent to the first insertion hole, and in which a second insertion part of another one of the two medical instruments can be inserted in the inside of the penetration part along a direction parallel to the first insertion hole so as to be freely movable back and forth;

a first slit type airtight valve which is provided in the first insertion hole and includes a first slit configured to maintain airtightness when the first insertion part is removed from the first insertion hole;

a second slit type airtight valve which is provided in the second insertion hole and includes a second slit configured to maintain airtightness when the second insertion part is removed from the second insertion hole;

a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein:

the first slit type airtight valve and the second slit type airtight valve are adjacently disposed via a partition wall, and, when the first slit type airtight valve and the second slit type airtight valve are projected on a surface orthogonal to the first insertion hole, the first slit type airtight valve and the second slit type airtight valve are formed in a line-symmetric shape centering on a reference line passing through a center of the first insertion hole and a center of the second insertion hole;

a distance from the center of the first insertion hole to a wall core of the partition wall is formed to be shorter than a distance from the center of the first insertion hole to an edge part thereof on a side opposite to the partition wall, and a distance from the center of the second insertion hole to the wall core of the partition wall is formed to be shorter than a distance from the center of the second insertion hole to an edge part thereof on a side opposite to the partition wall; and the first slit and the second slit are disposed along the reference line in the surface orthogonal to the first insertion hole.

What is claimed is:

1. An outer tube comprising:

a penetration part configured to include a distal end, a proximal end and a longitudinal axis, and to penetrate a body wall;

a first insertion hole in which a first insertion part of one of two medical instruments to be inserted inside the penetration part can be inserted in the inside of the penetration part along a direction parallel to the longitudinal axis so as to be freely movable back and forth;

a second insertion hole which is disposed adjacent to the first insertion hole via a partition wall, and in which a second insertion part of another one of the two medical instruments can be inserted in the inside of the penetration part along a direction parallel to the first insertion hole so as to be freely movable back and forth;

a first slit type airtight valve which is provided in the first insertion hole and includes a first slit configured to maintain airtightness when the first insertion part is removed from the first insertion hole;

a second slit type airtight valve which is provided in the second insertion hole and includes a second slit configured to maintain airtightness when the second insertion part is removed from the second insertion hole;

a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein:

when the first insertion hole and the second insertion hole are projected on a surface orthogonal to the first insertion hole, the first insertion hole and the second insertion hole are formed in a line-symmetric shape centering on a reference line passing through a center of the first insertion hole and a center of the second insertion hole, and, in the surface orthogonal to the first insertion hole, a distance from the center of the first insertion hole to a wall core of the partition wall is formed to be shorter than a distance from the center of the first insertion hole to an edge part thereof on a side opposite to the partition wall, and a distance from the center of the second insertion hole to the wall core of the partition wall is formed to be shorter than a distance from the center of the second insertion hole to an edge part thereof on a side opposite to the partition wall.

2. The outer tube according to claim 1, wherein the partition wall is formed in a tabular shape.

3. The outer tube according to claim 1, wherein, when the first insertion hole and the second insertion hole are projected on the surface orthogonal to the first insertion hole, the first insertion hole and the second insertion hole are formed in a D-shape having a straight edge and an arc edge.

4. The outer tube according to claim 1, wherein each of the first slit and the second slit has a cross shape, and a longer slit of two slits forming the cross-shaped slit functions as the first slit and the second slit.

5. The outer tube according to claim 1, wherein an insertion member having the first insertion hole and the second insertion hole is provided between the first slit type airtight valve and the first opening type airtight valve, and between the second slit type airtight valve and the second opening type airtight valve.

6. The outer tube according to claim 5, further comprising an introduction part disposed in a proximal end of the penetration part, wherein the first slit type airtight valve, the second slit type airtight valve, the first opening type airtight valve, the second opening type airtight valve and the insertion member are provided in the introduction part.

7. The outer tube according to claim 5, wherein the first slit type airtight valve, the second slit type airtight valve, the first opening type airtight valve, the second opening type airtight valve and the insertion member are formed as an integrated unit valve body.

8. The outer tube according to claim 1, wherein the first insertion part is an insertion part of an endoscope and the second insertion part is an insertion part of a treatment tool.

9. The outer tube according to claim 8, wherein a diameter of the first opening of the first opening type airtight valve is larger than a diameter of the second opening of the second opening type airtight valve.

10. The outer tube according to claim 1 wherein the first slit type airtight valve and the second opening type airtight valve are integrally formed, and the second slit type airtight valve and the first opening type airtight valve are integrally formed.

11. The outer tube according to claim 1 wherein the first slit type airtight valve and the second slit type airtight valve are integrally formed, and the first opening type airtight valve and the second opening type airtight valve are integrally formed.

12. An outer tube comprising:

a penetration part configured to include a distal end, a proximal end and a longitudinal axis, and to penetrate a body wall;

a first insertion hole in which a first insertion part of one of two medical instruments to be inserted inside the penetration part can be inserted in the inside of the penetration part along a direction parallel to the longitudinal axis so as to be freely movable back and forth;

a second insertion hole which is disposed adjacent to the first insertion hole, and in which a second insertion part of another one of the two medical instruments can be inserted in the inside of the penetration part along a direction parallel to the first insertion hole so as to be freely movable back and forth;

a first slit type airtight valve which is provided in the first insertion hole and includes a first slit configured to maintain airtightness when the first insertion part is removed from the first insertion hole;

a second slit type airtight valve which is provided in the second insertion hole and includes a second slit configured to maintain airtightness when the second insertion part is removed from the second insertion hole;

a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein:

the first slit type airtight valve and the second slit type airtight valve are disposed in mutually shifted positions in an axial direction of the longitudinal axis of the penetration part on opposite sides of the first and second insertion holes.

13. The outer tube according to claim 12, wherein the first slit type airtight valve and the second opening type airtight valve are integrally formed, and the second slit type airtight valve and the first opening type airtight valve are integrally formed.

14. An outer tube comprising:

a penetration part configured to include a distal end, a proximal end and a longitudinal axis, and to penetrate a body wall;

a first insertion hole in which a first insertion part of one of two medical instruments to be inserted inside the penetration part can be inserted in the inside of the penetration part along a direction parallel to the longitudinal axis so as to be freely movable back and forth;

a second insertion hole which is disposed adjacent to the first insertion hole via a partition wall, and in which a second insertion part of another one of the two medical instruments can be inserted in the inside of the penetration part along a direction parallel to the first insertion hole so as to be freely movable back and forth;

a first slit type airtight valve which is provided in the first insertion hole and includes a first slit configured to maintain airtightness when the first insertion part is removed from the first insertion hole;

a second slit type airtight valve which is provided in the second insertion hole and includes a second slit configured to maintain airtightness when the second insertion part is removed from the second insertion hole;

a first opening type airtight valve which is provided in the first insertion hole and includes a first opening configured to closely contact with an outer peripheral part of the first insertion part to maintain airtightness when the first insertion part is inserted in the first insertion hole; and a second opening type airtight valve which is provided in the second insertion hole and includes a second opening configured to closely contact with an outer peripheral part of the second insertion part to maintain airtightness when the second insertion part is inserted in the second insertion hole, wherein:

the first insertion hole and the second insertion hole have a major axis and a minor axis in a cross-section orthogonal to the longitudinal axis of the penetration part, and the first slit and the second slit are formed along the minor axis.

* * * * *